United States Patent
Shirude et al.

(10) Patent No.: US 11,124,494 B2
(45) Date of Patent: Sep. 21, 2021

(54) ARYL HETEROCYCLIC PIPERIDINONE FORMYL PEPTIDE 2 RECEPTOR AND FORMYL PEPTIDE 1 RECEPTOR AGONISTS

(71) Applicant: Bristol-Myers Squibb Company, Princeton, NJ (US)

(72) Inventors: Pravin Sudhakar Shirude, Bangalore (IN); Amit Kumar Chattopadhyay, Bangalore (IN); Nicholas R. Wurtz, Pennington, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 7 days.

(21) Appl. No.: 16/619,965

(22) PCT Filed: Jun. 8, 2018

(86) PCT No.: PCT/US2018/036627
§ 371 (c)(1),
(2) Date: Dec. 6, 2019

(87) PCT Pub. No.: WO2018/227061
PCT Pub. Date: Dec. 13, 2018

(65) Prior Publication Data
US 2021/0078971 A1 Mar. 18, 2021

Related U.S. Application Data

(60) Provisional application No. 62/517,204, filed on Jun. 9, 2017.

(51) Int. Cl.
*C07D 401/12* (2006.01)
*C07D 211/56* (2006.01)
*C07D 413/10* (2006.01)

(52) U.S. Cl.
CPC .......... *C07D 401/12* (2013.01); *C07D 211/56* (2013.01); *C07D 413/10* (2013.01)

(58) Field of Classification Search
CPC .. C07D 401/12; C07D 413/10; C07D 405/10; C07D 211/76; A61K 31/45; A61K 31/451; A61K 31/506; A61K 31/5377
See application file for complete search history.

(56) References Cited

U.S. PATENT DOCUMENTS

| | | | |
|---|---|---|---|
| 9,822,069 B2 | 11/2017 | Takahashi et al. | |
| 10,029,983 B2 | 7/2018 | Takahashi et al. | |
| 10,252,992 B2 | 4/2019 | Takahashi et al. | |
| 10,464,891 B2 | 11/2019 | Takahashi et al. | |

FOREIGN PATENT DOCUMENTS

| | | |
|---|---|---|
| WO | WO2006063113 A2 | 6/2006 |
| WO | WO2016189876 A1 | 12/2016 |
| WO | WO2016189877 A1 | 12/2016 |
| WO | WO2017091496 A1 | 6/2017 |
| WO | WO2017100390 A1 | 6/2017 |
| WO | WO2018227058 A9 | 12/2018 |
| WO | WO2018227065 A1 | 12/2018 |
| WO | WO2018227067 A1 | 12/2018 |
| WO | WO2019173182 A1 | 9/2019 |

OTHER PUBLICATIONS

Klapars et al., "A General and Efficient Copper Catalyst for the Amidation of Aryl Halides", J. Am. Chem. Soc. 2002, 124, 7421-7428.
Yin et al., "Palladium-Catalyzed Intermolecular Coupling of Aryl Halides and Amides" Organic Letters vol. 2(8) 1101-1104 (2000).
Yin, et al., "Pd-Catalyzed Intermolecular Amidation of Aryl Halides: The Discovery that Xantphos Can Be Trans-Chelating in a Palladium Complex", J. Am. Chem. Soc. 2002, 124, 6043-6048.
Allen, Jr., Loyd V., "Remington: The Science and Practice of Pharmacy, vol. I and vol. II. Twenty-second edition", Pharmaceutical Press, 2012, p. 2724.
Chandrasekharan et al., "Lipoxins: nature's way to resolve inflammation", Journal of Inflammation Research, 2015:8 181-192.
Fredman et al., " Targeted nanoparticles containing the proresolvingpeptide Ac2-26 protect against advancedatherosclerosis in hypercholesterolemic mice", Sci. Trans. Med., 2015, 7(275); pp. 275ra20).
Gavins, Felicity N,E., "Are formyl peptide receptors novel targets for therapeutic intervention ischaemia-reperfusion injury?" Trends in Pharmacological Sciences, vol. 31(6), pp. 266-276 (2010).
Greene, T.W. et al., Protecting Groups in Organic Synthesis, 4th Edition, Wiley (2007)).
Kain et al., "Resolvin D1 activates the inflammation resolving response at splenic and ventricular site following myocardial infarction leading to improved ventricular function", Journal of Molecular and Cellular Cardiology, vol. 84, pp. 24-35 (2015).
Kiyomor, et al., "An Efficient Copper-Catalyzed Coupling of Aryl Halides with Imidazoles", Tetrahedron Letters 40 (1999) 2657-2660.
Klapars, et al., "A General and Efficient Copper Catalyst for theAmidation of Aryl Halides and the N-Arylation of Nitrogen Heterocycles", J. Am. Chem. Soc. 2001, 123, 7727-7729.

(Continued)

*Primary Examiner* — Deepak R Rao
(74) *Attorney, Agent, or Firm* — Hong Liu

(57) ABSTRACT

The disclosure relates to compounds of formula (I), which are formyl peptide 2 (FPR2) receptor agonists and/or formyl peptide 1 (FPR1) receptor agonists. The disclosure also provides compositions and methods of using the compounds, for example, for the treatment of atherosclerosis, heart failure, and related diseases.

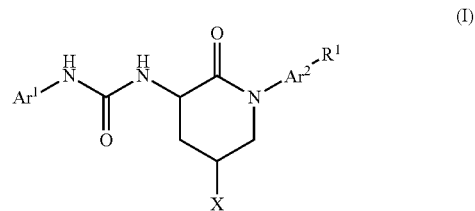

7 Claims, No Drawings

(56) References Cited

OTHER PUBLICATIONS

Liu et al., "Lipoxin A4 ameliorates ischemia/reperfusion induced spinal cord injury in rabbit model", Int. J. Clin.Exp. Medicine, Vo. 8(8), pp. 12826-12833 (2015.
Perretti, et al., "Resolution Pharmacology:Opportunities for Therapeutic Innovationin Inflammation", Trends in Pharmacological Sciences,vol. 36(11) 2015.
Petri et al., "The role of the FPR2/ALX receptor in atherosclerosis development and plaque stability", Cardiovascular Research, vol. 105, pp. 65-74 (2015).
Romano et al., "Lipoxins and aspirin-triggered lipoxinsin resolution of inflammation", European Journal of Pharmacology vol. 760 pp. 49-63 (2015).
Shaughnessy, et al., "Copper-Catalyzed Amination of Aryl and Alkenylelectrophiles", Organic Reactions, vol. 85(1), pp. 1-668 (2014).
Surry, et al. "Biaryl Phosphane Ligands in Palladium-CatalyzedAmination", Angew.Chem.Int.Ed. vol. 47,6338-6361 (2008).
Surry, et al., "Dialkylbiaryl Phosphines in Pd-Catalyzed Amination: A User's Guide", Chem Sci. vol. 2(1): 27-50 (2011).
Ye et al., "International Union of Basic and Clinical Pharmacology. LXXIII. Nomenclature for the Formyl Peptide Receptor (FPR) Family", Pharmacological Reviews, vol. 61(2), 2009.

ARYL HETEROCYCLIC PIPERIDINONE FORMYL PEPTIDE 2 RECEPTOR AND FORMYL PEPTIDE 1 RECEPTOR AGONISTS

CROSS-REFERENCE TO RELATED APPLICATION

This application is a 371 application of PCT/US2018/036627 filed Jun. 8, 2018, which claims the benefit of U.S. Provisional Application Ser. No. 62/517,204 filed on Jun. 9, 2017, which is hereby incorporated by reference in its entirety.

BACKGROUND OF THE INVENTION

The present invention relates to novel piperidinone compounds, which are formyl peptide 2 (FPR2) receptor agonists and/or formyl peptide 1 (FPR1) receptor agonists, compositions containing them, and methods of using them, for example, for the treatment of atherosclerosis, heart failure, chronic obstructive pulmonary disease (COPD), and related diseases.

Formyl peptide receptor 2 (FPR2) belongs to small group of seven-transmembrane domain, G protein-coupled receptors that are expressed mainly by mammalian phagocytic leukocytes and are known to be important in host defense and inflammation. FPR2 shares significant sequence homology with FPR1 and FPR3. Collectively, these receptors bind large number of structurally diverse group of agonists, including N-formyl and nonformyl peptides which act as chemo attractants and activate phagocytes. The endogenous anti-inflammatory peptide Annexin A1 and its N-terminal fragments also bind human FPR1 and FPR2. Importantly, anti-inflammatory eicosanoid lipoxin A4, which belongs to newly discovered class of small pro-resolution mediators (SPMs), has been identified as a specific agonist for FPR2 (Ye R D., et al., Pharmacol. Rev., 2009, 61, 119-61).

Endogenous FPR2 pro-resolution ligands, such as lipoxin A4 and Annexin A1 bind to the receptor triggering a wide array of cytoplasmatic cascades such as Gi coupling, $Ca^{2+}$ mobilization and □-arrestin recruitment. Activation of FPR2 by lipoxin A4 modifies the effects of peptidic agonists, such as serum amyloid A (SAA), and has alternative effects on phosphorylation pathways depending on the cell type. Lipoxins regulate components of both innate and adaptive immune systems including neutrophils, macrophages, T-, and B-cells. In neutrophils, lipoxins modulate their movement, cytotoxicity and life span. In macrophages, lipoxins prevent their apoptosis and enhance efferocytosis. In most inflammatory cells, lipoxins also down-regulate expression of several pro-inflammatory cytokines, such as IL-6, IL-1□ and IL-8 as well as up-regulate expression of anti-inflammatory cytokine IL-10 (Chandrasekharan J A, Sharma-Walia N., J. Inflamm. Res., 2015, 8, 181-92). The primary effects of lipoxin on neutrophils and macrophages are termination of inflammation and initiation of resolution of inflammation. The latter is primarily responsible for enhancing anti-fibrotic wound healing and returning of the injured tissue to homeostasis (Romano M., et al., Eur. J. Pharmacol., 2015, 5, 49-63).

Chronic inflammation is part of the pathway of pathogenesis of many human diseases and stimulation of resolution pathways with FPR2 agonists may have both protective and reparative effects. Ischaemia-reperfusion (I/R) injury is a common feature of several diseases associated with high morbidity and mortality, such as myocardial infarction and stroke. Non-productive wound healing associated with cardiomyocyte death and pathological remodeling resulting from ischemia-reperfusion injury leads to scar formation, fibrosis, and progressive lost of heart function. FPR2 modulation is proposed to enhance myocardial wound healing post injury and diminish adverse myocardial remodeling (Kain V., et al., J. Mol. Cell. Cardiol., 2015, 84, 24-35). In addition, FPR2 pro-resolution agonists, in the central nervous system, may be useful therapeutics for the treatment of a variety of clinical I/R conditions, including stroke in brain (Gavins F N., Trends Pharmacol. Sci., 2010, 31, 266-76) and I/R induced spinal cord injury (Liu Z Q., et al., Int. J. Clin. Exp. Med., 2015, 8, 12826-33).

In addition to beneficial effects of targeting the FPR2 with novel pro-resolution agonists for treatment of I/R induced injury therapeutic, utility of these ligands can also be applied to other diseases. In the cardiovascular system both the FPR2 receptor and its pro-resolution agonists were found to be responsible for atherogenic-plaque stabilization and healing (Petri M H., et al., Cardiovasc. Res., 2015, 105, 65-74; and Fredman G., et al., Sci. Trans. Med., 2015, 7(275); 275ra20). FPR2 agonists also have been shown to be beneficial in preclinical models of chronic inflammatory human diseases, including: infectious diseases, psoriasis, dermatitis, occular inflammation, sepsis, pain, metabolic/diabetes diseases, cancer, COPD, asthma and allergic diseases, cystic fibrosis, acute lung injury and fibrosis, rheumatoid arthritis and other joint diseases, Alzheimer's disease, kidney fibrosis, and organ transplantation (Romano M., et al., Eur. J. Pharmacol., 2015, 5, 49-63, Perrett, M., et al., Trends in Pharm. Sci., 2015, 36, 737-755).

DESCRIPTION OF THE INVENTION

The invention encompasses compounds of formula I, which are formyl peptide 2 (FPR2) receptor agonists and/or formyl peptide 1 (FPR1) receptor agonists, compositions containing them, and methods of using them, for example, in the treatment of atherosclerosis, heart failure, chronic obstructive pulmonary disease (COPD), and related diseases.

One aspect of the invention is a compound of formula I

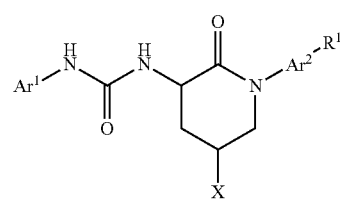

where:
$Ar^1$ is phenyl, pyridinyl, pyridazinyl, pyrimidinyl, pyrazinyl, or benzodioxyl, and is substituted with 1-3 substituents selected from cyano, halo, alkyl, haloalkyl, alkoxy, haloalkoxy, alkylthio, and alkylsulfonyl;
$Ar^2$ is phenyl, pyridinyl, pyridazinyl, pyrimidinyl, or pyrazinyl, and is substituted with 0-3 substituents selected from cyano, halo, alkyl, haloalkyl, alkoxy, and haloalkoxy;
$Ar^3$ is 5- or 6-membered monocyclic heteroaromatic ring system with 1-5 heteroatoms independently selected from nitrogen, oxygen, and sulfur;
$R^1$ is cyclopropyl, cyclobutyl, cyclopentyl, cyclohexyl, tetrahyrofuranyl, or tetrahydropyranyl, and is substituted with 0-2 substituents selected from cyano, alkyl, fluoroalkyl, hydroxyalkyl, alkoxyalkyl, ((R²)(R³)N)alkyl, hydroxy, alkoxy, (R²)(R³)N, (R²)(R³)NCO, and Ar³;
R² is hydrogen, alkyl, alkylcarbonyl, or alkylsulfonyl;
R³ is hydrogen or alkyl;
or NR²R³ taken together is selected from azetidinyl, pyrrolidinyl, piperidinyl, piperazinyl, and morpholinyl, and is substituted with 0-3 substituents selected from fluoro, alkyl, haloalkyl, alkoxy, and fluoroalkoxy; and
X is hydrogen, fluoro, hydroxy, or alkoxy;
or a pharmaceutically acceptable salt thereof.

Another aspect of the invention is a compound of formula I where
Ar¹ is phenyl, pyrazinyl or pyridinyl and is substituted with 1-3 substituents selected from cyano, halo, alkyl, haloalkyl, alkoxy, fluoroalkoxy, alkylthio, and alkylsulfonyl;
Ar² is phenyl or pyridinyl and is substituted with 0-3 substituents selected from cyano, halo, alkyl, haloalkyl, alkoxy, and haloalkoxy;
Ar³ is 5- or 6-membered monocyclic heteroaromatic ring system with 1-5 heteroatoms independently selected from nitrogen, oxygen, and sulfur;
R¹ is cyclopropyl, cyclobutyl, cyclopentyl, cyclohexyl, tetrahyrofuranyl, or tetrahydropyranyl, and is substituted with 0-2 substituents selected from cyano, alkyl, fluoroalkyl, hydroxyalkyl, alkoxyalkyl, ((R²)(R³)N)alkyl, hydroxy, alkoxy, (R²)(R³)N, (R²)(R³)NCO, and Ar³;
R² is hydrogen, alkyl, alkylcarbonyl, or alkylsulfonyl;
R³ is hydrogen or alkyl;
or NR²R³ taken together is selected from azetidinyl, pyrrolidinyl, piperidinyl, piperazinyl, and morpholinyl, and is substituted with 0-3 substituents selected from halo, alkyl, haloalkyl, alkoxy, and haloalkoxy; and
X is hydrogen, fluoro, hydroxy, or alkoxy;
or a pharmaceutically acceptable salt thereof.

Another aspect of the invention is a compound of formula I where Ar¹ is phenyl or pyridinyl and is substituted with 1-3 substituents selected from cyano, halo, alkyl, haloalkyl, alkoxy, haloalkoxy, alkylthio, and alkylsulfonyl.

Another aspect of the invention is a compound of formula I where Ar² is phenyl or pyridinyl and is substituted with 0-3 substituents selected from cyano, halo, alkyl, haloalkyl, alkoxy, and haloalkoxy.

Another aspect of the invention is a compound of formula I where Ar³ is 5-membered monocyclic heteroaromatic ring system with 1-3 heteroatoms independently selected from nitrogen, oxygen, and sulfur.

Another aspect of the invention is a compound of formula I where Ar³ is 6-membered monocyclic heteroaromatic ring system with 1-3 nitrogen atoms.

Another aspect of the invention is a compound of formula I where R¹ is cyclopropyl, cyclobutyl, cyclopentyl, cyclohexyl, tetrahyrofuranyl, or tetrahydropyranyl, and is substituted with 0-2 substituents selected from cyano, ((R²)(R³)N)alkyl, and hydroxy.

For a compound of Formula I, the scope of any instance of a variable substituent, including Ar¹, Ar², Ar³, R¹, R², R³, and X can be used independently with the scope of any other instance of a variable substituent. As such, the invention includes combinations of the different aspects.

Unless specified otherwise, these terms have the following meanings. "Alkyl" means a straight or branched alkyl group composed of 1 to 6 carbons. "Alkenyl" means a straight or branched alkyl group composed of 2 to 6 carbons with at least one double bond. "Alkynyl" means a straight or branched alkyl group composed of 2 to 6 carbons with at least one triple bond. "Cycloalkyl" means a monocyclic ring system composed of 3 to 7 carbons. Terms with a hydrocarbon moiety (e.g. alkoxy) include straight and branched isomers for the hydrocarbon portion. "Halo" includes fluoro, chloro, bromo, and iodo. "Haloalkyl" and "haloalkoxy" include all halogenated isomers from monohalo to perhalo. "Aryl" means a monocyclic or bicyclic aromatic hydrocarbon group having 6 to 12 carbon atoms. Bicyclic ring systems can consist of a phenyl group fused to a aromatic or non-aromatic carbocyclic ring. Representative examples of aryl groups include but are not limited to phenyl, indanyl, indenyl, naphthyl, and tetrahydronaphthyl. "Heteroaryl" means a 5 to 7 membered monocyclic or 8 to 11 membered bicyclic aromatic ring system with 1-5 heteroatoms independently selected from nitrogen, oxygen, and sulfur. Where a bonding attachment location is not specified, the bonding may be attached at any appropriate location as understood by practitioners in the art. Combinations of substituents and bonding patterns are only those that result in stable compounds as understood by practitioners in the art. Parenthetic and multiparenthetic terms are intended to clarify bonding relationships to those skilled in the art. For example, a term such as ((R)alkyl) means an alkyl substituent further substituted with the substituent R.

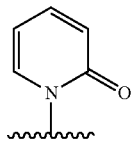

Heteroaryl includes N-subsituted pyridinonyl

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the invention exist in stereoisomeric forms. The invention includes all stereoisomeric forms of the compounds including enantiomers and diastereomers. Methods of making and separating stereoisomers are known in the art. The invention includes all tautomeric forms of the compounds. The invention includes atropisomers and rotational isomers.

The invention is intended to include all isotopes of atoms occurring in the compounds. Isotopes include those atoms having the same atomic number but different mass numbers. By way of general example and without limitation, isotopes of hydrogen include deuterium and tritium. Isotopes of carbon include ¹³C and ¹⁴C. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

Biological Methods

N-formyl peptide receptors (FPRs) are a family of chemo attractant receptors that facilitate leukocyte response during inflammation. FPRs belong to the seven-transmembrane G protein-coupled receptor superfamily and are linked to inhibitory G-proteins (Gi). Three family members (FPR1, FPR2 and FPR3) have been identified in humans and are predominantly found in myeloid cells with varied distribution and have also been reported in multiple organs and tissues. After agonist binding, the FPRs activate a multitude of physiological pathways, such as intra cellular signaling transduction, Ca2+ mobilization and transcription. The family interacts with a diverse set of ligands that includes proteins, polypeptides and fatty acid metabolites which activate both pro-inflammatory and pro-resolution downstream responses.

The FPR2 receptor binds multiple ligands to invoke both inflammatory and anti-inflammatory responses. Inflammation mediator release by FPR2 is promoted by endogenous protein ligands such as Serum amyloid A (SAA) and Amyloid □ (1-42), whereas resolution of inflammation is induced by ligands that include arachidonic acid metabolites, lipoxin A4 (LXA4) and Epi-lipoxin (ATL), and a docosahexenoic acid metabolite, resolvin D1 (RvD1). The pro-resolving fatty acid metabolites mediate inhibition and resolution of inflammation through the FPR2 receptor by stimulating phagocytosis of apotic neutrophils by macrophages. Removal of the apotic neutrophils induce the release of cytokines that activate pro-resolution pathways.

The FPR1 receptor was originally isolated as a high affinity receptor for N-Formylmethionine containing peptides, such as N-Formylmethionine-leucyl-phenylalanine (FMLP). The protein directs mammalian phagocytic and blood leukocyte cells to sites of invading pathogens or inflamed tissues and activates these cells to kill pathogens or to remove cellular debris.

FPR2 and FPR1 Cyclic Adenosine Monophosphate (cAMP) Assays. A mixture of forskolin (5 µM final for FPR2 or 10 µM final for FPR1) and IBMX (200 µM final) were added to 384-well Proxiplates (Perkin-Elmer) pre-dotted with test compounds in DMSO (1% final) at final concentrations in the range of 1.7 nM to 100 µM. Chinese Hamster Ovary cells (CHO) overexpressing human FPR1 or human FPR2 receptors were cultured in F-12 (Ham's) medium supplemented with 10% qualified FBS, 250 µg/ml zeocin and 300 µg/ml hygromycin (Life Technologies). Reactions were initiated by adding 2,000 human FPR2 cells per well or 4,000 human FPR1 cells per well in Dulbecco's PBS (with calcium and magnesium) (Life Technologies) supplemented with 0.1% BSA (Perkin-Elmer). The reaction mixtures were incubated for 30 min at room temperature. The level of intracellular cAMP was determined using the HTRF HiRange cAMP assay reagent kit (Cisbio) according to manufacturer's instruction. Solutions of cryptate conjugated anti-cAMP and d2 flurorophore-labelled cAMP were made in a supplied lysis buffer separately. Upon completion of the reaction, the cells were lysed with equal volume of the d2-cAMP solution and anti-cAMP solution. After a 1-h room temperature incubation, time-resolved fluorescence intensity was measured using the Envision (Perkin-Elmer) at 400 nm excitation and dual emission at 590 nm and 665 nm. A calibration curve was constructed with an external cAMP standard at concentrations ranging from 1 µM to 0.1 pM by plotting the fluorescent intensity ratio from 665 nm emission to the intensity from the 590 nm emission against cAMP concentrations. The potency and activity of a compound to inhibit cAMP production was then determined by fitting to a 4-parametric logistic equation from a plot of cAMP level versus compound concentrations.

The examples disclosed below were tested in the FPR2 and FPR1 cAMP assay described above and found having FPR2 and/or FPR1 agonist activity. A range of $IC_{50}$ values of 1.25 µM (1250 nM) in one of the assays was observed. Table 1 below lists $EC_{50}$ values in the FPR2 and FPR1 cAMP assays measured for the following examples.

TABLE 1

| Example | hFPR2 cAMP2 $EC_{50}$ (uM) | hFPR1 cAMP EC50 (uM) |
| --- | --- | --- |
| 6 | 0.00070 | 0.10 |
| 18 | 0.00017 | 0.0020 |
| 27 | 0.00091 | 0.13 |
| 41 | 0.98 | 7.6 |
| 42 | 0.00021 | 0.033 |
| 52 | 0.017 | 0.56 |
| 53 | 0.017 | 0.70 |
| 57 | 0.96 | >5,000 |
| 58 | 1.0 | 3.4 |
| 62 | 1.2 | 1.1 |
| 69 | 0.019 | 0.66 |
| 71 | 0.017 | 2.1 |
| 73 | 83 | 330 |
| 77 | 3.2 | 3.6 |

The following Examples were tested in the hFPR2 Assay described above and found having hFPR2 agonist activity with $EC_{50}$ values of ≤0.010 µM (10 nM): 1, 2, 5, 7, 8, 9, 12, 14, 19, 20, 23, 24, 25, 28, 31, 33, 36, 39, 46, 49, 50, 51, 55.

The following Examples were tested in the hFPR2 Assay described above and found having hFPR2 agonist activity with $EC_{50}$ values between 0.010 µM and 0.100 µM: 4, 10, 13, 15, 16, 17, 21, 26, 29, 34, 37, 40, 43, 63, 64, 68, 70.

The following Examples were tested in the hFPR2 Assay described above and found having hFPR2 agonist activity with $EC_{50}$ values between 0.10 µM and 1.25 µM: 3, 11, 22, 30, 32, 35, 38, 45, 47, 48, 54, 56, 59, 60, 61, 65, 66, 67.

Pharmaceutical Compositions and Methods of Use

The compounds of the present invention may be administered to patients for the treatment of a variety of conditions and disorders, including atherosclerosis, heart failure, lung diseases including asthma, COPD, cystic fibrosis, neuroinflammatory diseases including multiple sclerosis, Alzheimer's disease, stroke, and chronic inflammatory diseases such as inflammatory bowel disease, rheumatoid arthritis, psoriasis, sepsis, lupus, and kidney fibrosis.

Another aspect of the invention is a pharmaceutical composition comprising a therapeutically effective amount of a compound of formula I in combination with a pharmaceutical carrier.

Another aspect of the invention is a pharmaceutical composition comprising a therapeutically effective amount of a compound of formula I in combination with at least one other therapeutic agent and a pharmaceutical carrier.

Unless otherwise specified, the following terms have the stated meanings. The term "patient" means a subject suitable for therapy as determined by practitioners in the field and encompasses all suitable mammalian species including humans that could potentially benefit from treatment with a FPR2 and/or FPR1 agonist as understood by practioners in this field. Common risk factors include, but are not limited to, age, sex, weight, family history, sleep apnea, alcohol or tobacco use, physical inactivity arrthymia or signs of insulin resistance such as acanthosis nigricans, hypertension, dyslipidemia, or polycystic ovary syndrome (PCOS). "Treating" or "treatment" encompass the treatment of a patient as understood by practitioners in the art and include inhibiting the disease-state, i.e., arresting it development; relieving the disease-state, i.e., causing regression of the disease state; and/or preventing the disease-state from occurring in a patient. "Therapeutically effective amount" is intended to include an amount of a compound that is effective or beneficial as understood by practitioners in this field.

"Pharmaceutical composition" means a composition comprising a compound of the invention in combination with at least one additional pharmaceutically acceptable carrier. A "pharmaceutically acceptable carrier" refers to media for the delivery of biologically active agents as understood by practitioners in the art, such as diluents, preserving agents, fillers, flow regulating agents, disintegrating agents, wetting agents, emulsifying agents, suspending agents, sweetening agents, flavoring agents, perfuming agents, anti-bacterial agents, anti-fungal agents, lubricating agents, and dispensing agents. Pharmaceutically acceptable carriers are formulated according to a number of factors known to those of ordinary skill in the art. These include, without limitation, the type and nature of the active agent being formulated; the subject to which the agent-containing composition is to be administered; the intended route of administration of the composition; and the therapeutic indication being targeted. Descriptions of suitable pharmaceutically acceptable carriers and factors involved in their selection are known in the art in such references as Allen, L. V., Jr. et al., *Remington: The Science and Practice of Pharmacy* (2 Volumes), 22nd Edition, Pharmaceutical Press (2012).

Solid compositions are normally formulated in dosage units and compositions providing form about 1 to 1000 mg of the active ingredient per dose are preferred. Some examples of dosages are 1 mg, 10 mg, 100 mg, 250 mg, 500 mg, and 1000 mg.

Liquid compositions are usually in dosage unit ranges. Generally, the liquid composition will be in a unit dosage range of 1-100 mg/mL. Some examples of dosages are 1 mg/mL, 10 mg/mL, 25 mg/mL, 50 mg/mL, and 100 mg/mL.

Another aspect of the invention is a method for treating heart disease comprising administering a therapeutically effective amount of a compound of formula I to a patient.

Another aspect of the invention is a method for treating heart disease wherein the heart disease is selected from the group consisting of angina pectoris, unstable angina, myocardial infarction, heart failure, acute coronary disease, acute heart failure, chronic heart failure, and cardiac iatrogenic damage.

Another aspect of the invention is a method for treating heart disease wherein the treatment is post myocardial infarction.

Another aspect of the invention is the method wherein the heart disease is associated with chronic heart failure.

Another aspect of the invention is the method wherein the treatment is to improve myocardial wound healing.

Another aspect of the invention is the method wherein the treatment is to diminish myocardial fibrosis.

The invention encompasses all conventional modes of administration; oral and parenteral methods are preferred. Generally, the dosing regimen will be similar to other cardiovascular agents used clinically. The dosage regimen and mode for administration for the compounds of the present invention will depend on known factors known by practitioners in the art and include age, sex, health, medical condition, and weight of the recipient; the nature and extent of the symptoms; the kind of concurrent treatment; the frequency of treatment; the route of administration, and the effect desired. Typically, the daily dose will be 0.1-100 mg/kg body weight daily. Generally, more compound is required orally and less parenterally. The specific dosing regimen, however, will be determined by a physician using sound medical judgment.

Another aspect of the invention is a method for treating heart disease comprising administering a therapeutically effective amount of a compound of formula I to a patient in conjunction with at least one other therapeutic agent.

The compounds of the present invention may be employed in combination with other suitable therapeutic agents useful in the treatment of the aforementioned diseases or disorders including: anti-atherosclerotic agents, anti-dyslipidemic agents, anti-diabetic agents, anti-hyperglycemic agents, anti-hyperinsulinemic agents, anti-thrombotic agents, anti-retinopathy agents, anti-neuropathic agents, anti-nephropathic agents, anti-ischemic agents, anti-hypertensive agents, anti-obesity agents, anti-hyperlipidemic agents, anti-hypertriglyceridemic agents, anti-hypercholesterolemic agents, anti-restenotic agents, anti-pancreatic agents, lipid lowering agents, anorectic agents, memory enhancing agents, anti-dementia agents, cognition promoting agents, appetite suppressants, agents for treating heart failure, agents for treating peripheral arterial disease, agents for treating malignant tumors, and anti-inflammatory agents.

The compounds of the invention may be used with one or more, preferable one to three, of the following heart failure agents selected from loop diuretics, Angiotensin converting enzyme (ACE) inhibitors, Angiotensin II receptor blockers (ARBs), angiotensin receptor-neprilysin inhibitors (ARNI), beta blockers, mineralocorticoid receptor antagonists, nitroxyl donors, RXFP1 agonists, APJ agonists and cardiotonic agents. These agents include, but are not limited to furosemide, bumetanide, torsemide, sacubitrial-valsartan, thiazide diuretics, captopril, enalapril, lisinopril, carvedilol, metopolol, bisoprolol, serelaxin, spironolactone, eplerenone, ivabradine, candesartan, eprosartan, irbestarain, losartan, olmesartan, telmisartan, and valsartan.

The compounds of the present invention are also useful as standard or reference compounds, for example as a quality standard or control, in tests or assays involving the FPR2. Such compounds may be provided in a commercial kit, for example, for use in pharmaceutical research involving FPR2 activity. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness. The compounds of the present invention may also be used in diagnostic assays involving FPR2.

Chemical Methods

Abbreviations as used herein, are defined as follows: "1×" for once, "2×" for twice, "3×" for thrice, "° C." for degrees Celsius, "aq" for aqueous, "Col" for column, "eq" for equivalent or equivalents, "g" for gram or grams, "mg" for milligram or milligrams, "L" for liter or liters, "mL" for milliliter or milliliters, "μL" for microliter or microliters, "N" for normal, "M" for molar, "nM" for nanomolar, "mol" for mole or moles, "mmol" for millimole or millimoles, "min" for minute or minutes, "h" for hour or hours, "rt" for room temperature, "RT" for retention time, "ON" for overnight, "atm" for atmosphere, "psi" for pounds per square inch, "conc." for concentrate, "aq" for "aqueous", "sat" or "sat'd" for saturated, "MW" for molecular weight, "mw" or "μwave" for microwave, "mp" for melting point, "Wt" for weight, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

| | |
|---|---|
| Ac | Acetic |
| AcOH | acetic acid |
| ACN (or MeCN) | acetonitrile |
| Bn | benzyl |
| Boc | tert-butyl carbonyl |
| Boc$_2$O | Di-tert-butyl dicarbonate |
| Bu | butyl |
| dba (Pd$_2$(dba)$_3$) | dibenzylideneacetone |
| DCM | dichloromethane |
| DIEA or DIPEA | diisopropylethylamine |
| DME | Dimethoxyethane |
| DMF | dimethylformamide |
| DMEDA | N,N'-dimethylethylenediamine |
| DMSO | dimethyl sulfoxide |
| dppf | 1,1'-bis(diphenylphosphino)ferrocene |
| Et | ethyl |
| EtOH | ethanol |
| EtOAc | ethyl acetate |
| i-Bu | isobutyl |
| i-Pr | isopropyl |
| Me | methyl |
| MeOH | methanol |
| NMP | N-Methylpyrrolidone |
| OAc | Acetate |
| Ph | phenyl |
| Pr | propyl |
| RuPhos | 2-dicyclohexylphosphino-2',6'-diipropoxy-1,1'-biphenyl |
| t-Bu | tert-butyl |
| TEA | Triethylamine |
| TFA | Trifluoroacetic acid |
| THF | tetrahydrofuran |

The compounds of this invention can be made by various methods known in the art including those of the following schemes and in the specific embodiments section. The structure numbering and variable numbering shown in the synthetic schemes are distinct from, and should not be confused with, the structure or variable numbering in the claims or the rest of the specification. The variables in the schemes are meant only to illustrate how to make some of the compounds of this invention.

The disclosure is not limited to the foregoing illustrative examples and the examples should be considered in all respects as illustrative and not restrictive, and all changes which come within the meaning and range of equivalency of the claims are therefore intended to be embraced.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene, T. W. et al., *Protecting Groups in Organic Synthesis*, 4th Edition, Wiley (2007)).

Compounds having the general Formula (IA): wherein rings A and B and C are defined above as Ar$^1$ and Ar$^2$, respectively, and can be prepared by the following one or more of the synthetic Schemes.

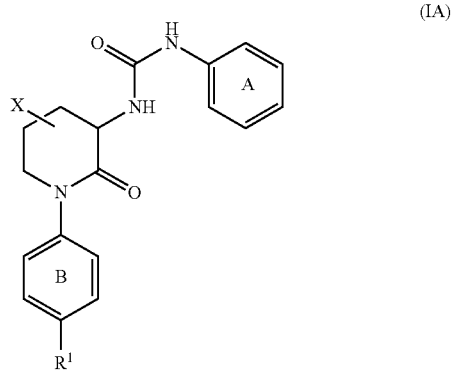

(IA)

1-Arylpiperidinone compounds of this invention wherein rings A and B are substituted phenyl or heteroaryl rings can be prepared by the general route shown in Scheme 1, starting from a suitably substituted aryl halide such as compound 1a. Palladium or copper-catalyzed coupling of 1a to a substituted suitably protected 3-aminopiperidin-2-one, where PG is a protecting group such as Boc or Cbz. Methods for this transformation include variations of Ullmann, Goldberg, and Buchwald copper-catalyzed amidation or Buchwald Pd-catalyzed amidation depending on the nature of ring B, using methods known to one skilled in the art for these types of couplings (see for example Yin & Buchwald *Organic Lett.* 2000, 2, 1101; Klapers et al. *JACS*, 2001, 123, 7727; Klapars et al. *JACS*, 2002, 124, 7421; Yin & Buchwald *JACS*. 2002, 124, 6043; Kiyomor, Madoux & Buchwald, *Tet. Lett.*, 1999, 40, 2657, Surry and Buchwald *Angew. Chem. Int Ed.*, 2008, 47, 6338, Surly & Buchwald *Chem Sci.* 2011; 2(1): 27-50; Shaughnessy, Ciganek & DeVasher, *Organic Reactions*. 2014, 85:1:1-668). Removal of the protecting group from 1b, followed by condensation of the resulting free amine with a suitably substituted aryl isocyanate, 1e or phenylcarbamate 1f can provide ureas 1d. Suitable isocyanates or phenylcarbamates are either commercially available or can be readily obtained from the corresponding aylamine by methods known to one skilled in the art. Alternately, the ureas 1d can be obtained by treatment of the deprotected 3-aminopiperidinone intermediate with 4-nitrophenylchloroformate to form the carbamate, followed by condensation with an appropriately substituted arylamine 1 g. It will also be recognized by one skilled in the art that additional compounds of this invention wherein rings A and B are heteroaryl rings, such as pyridine, pyrimidine, thiazole, etc., can also be prepared using the methods outlined in Scheme 1 by substituting the appropriate heteroaryl iodide or bromine for 1a and heteroaryl amine. Other aryl bromides that are substituted with heteroatom containing rings can be synthesized by those skilled in the art and be used in Scheme 1 to access other compounds of the invention. Substitution at R can be manipulated at intermediates 1a, 1b, 1c or 1d using synthetic methods known to those skilled in the art.

water. B=ACN/MeOH (or) Waters XBridge C18, 19×1500 mm, 5-μm particles; A=10 mM ammonium acetate in water. B=ACN/MeOH; Gradient: 0-100% B over 25 minutes, then a 5-minute hold at 100% B; Flow: 15 mL/min.

Unless otherwise stated, analysis of final products was carried out by reverse phase analytical HPLC.

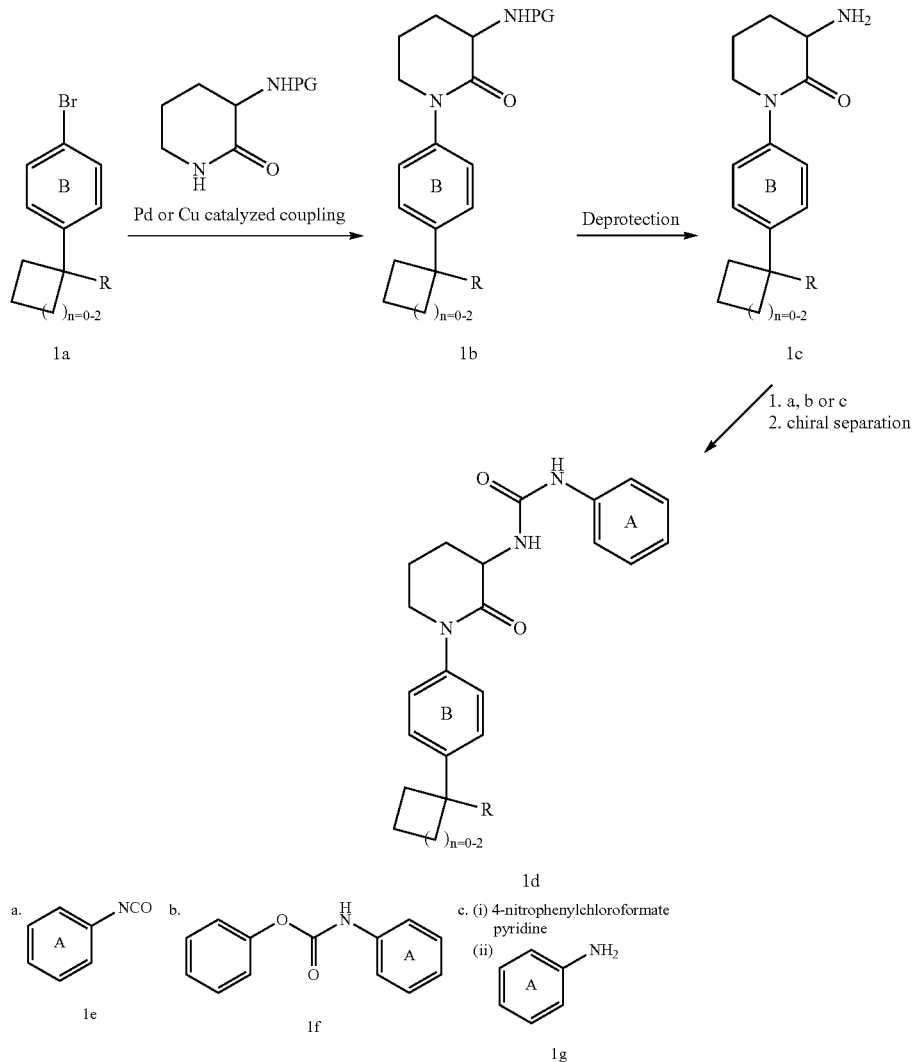

Scheme 1

The following methods were used in the exemplified Examples, except where noted otherwise. Purification of intermediates and final products was carried out via either normal or reverse phase chromatography. Normal phase chromatography was carried out using pre-packed $SiO_2$ cartridges eluting with either gradients of hexanes and EtOAc or DCM and MeOH unless otherwise indicated. Reverse phase preparative HPLC was carried out using C18 columns eluting with gradients of Solvent A (10 mM ammonium acetate in water) and Solvent B (ACN, UV 220 nm) or with gradients of Solvent A (10 mM ammonium acetate in water) and Solvent B (MeOH, UV 220 nm) or with gradients of Solvent A (0.1% TFA in water) and Solvent B (ACN, UV 220 nm) (or) SunFire Prep C18 OBD 5μ 19×150 mm, 25 min gradient from 0-100% B. A=10 mM ammonium acetate in Method A: SunFire C18 column (3.5 μm C18, 3.0×150 mm). Gradient elution (1.0 mL/min) from 10-100% Solvent B over 12 min and then 100% Solvent B for 3 min was used. Solvent A is 95% water, 5% acetonitrile, 0.05% TFA and Solvent B is 5% water, 95% acetonitrile, 0.05% TFA, UV 220 nm.

Method B: XBridge Phenyl column (3.5 μm C18, 3.0×150 mm). Gradient elution (1.0 mL/min) from 10-100% Solvent B over 12 min and then 100% Solvent B for 3 min was used. Solvent A is 95% water, 5% acetonitrile, 0.05% TFA and Solvent B is 5% water, 95% acetonitrile, 0.05% TFA, UV 220 nm.

Method C: Ascentis Express C18, 2.1×50 mm, 2.7-μm particles; Solvent A: 95% water, 5% acetonitrile, 0.05% TFA; Solvent B: 95% acetonitrile, 5% water, 0.1% TFA;

Temperature: 50° C.; Gradient: 0-100% B over 4 minutes, then a 1-minute hold at 100% B; Flow: 1.1 mL/min.

Method D: Ascentis Express C18, 2.1×50 mm, 2.7-μm particles; Solvent A: 95% water, 5% acetonitrile with 10 mM ammonium acetate; Solvent B: 95% acetonitrile, 5% water with 10 mM ammonium acetate; Temperature: 50° C.; Gradient: 0-100% B over 4 minutes, then a 1-minute hold at 100% B; Flow: 1.1 mL/min.

Method E: Ascentis Express C18, 2.1×50 mm, 2.7-μm particles; Solvent A: 95% water, 5% acetonitrile, 0.05% TFA; Solvent B: 95% acetonitrile, 5% water, 0.1% TFA; Temperature: 50° C.; Gradient: 0-100% B over 3 minutes, then a 1-minute hold at 100% B; Flow: 1.1 mL/min.

Method F: Ascentis Express C18, 2.1×50 mm, 2.7-μm particles; Solvent A: 95% water, 5% acetonitrile with 10 mM ammonium acetate; Solvent B: 95% acetonitrile, 5% water with 10 mM ammonium acetate; Temperature: 50° C.; Gradient: 0-100% B over 3 minutes, then a 1-minute hold at 100% B; Flow: 1.1 mL/min.

Method G: SunFire C18 column (3.5 μm C18, 3.0×150 mm). Gradient elution (1.0 mL/min) from 10-100% Solvent B over 25 min and then 100% Solvent B for 5 min was used. Solvent A is 95% water, 5% acetonitrile, 0.05% TFA and Solvent B is 5% water, 95% acetonitrile, 0.05% TFA, UV 220 nm.

Method H: XBridge Phenyl column (3.5 μm C18, 3.0×150 mm). Gradient elution (1.0 mL/min) from 10-100% Solvent B over 25 min and then 100% Solvent B for 5 min was used. Solvent A is 95% water, 5% acetonitrile, 0.05% TFA and Solvent B is 5% water, 95% acetonitrile, 0.05% TFA, UV 220 nm.

Method I: SunFire C18 column (3.5 μm, 4.6×150 mm). Gradient elution (1.0 mL/min) from 10-100% Solvent B over 12 min and then 100% Solvent B for 3 min was used. Solvent A is 95% water, 5% acetonitrile, 0.05% TFA and Solvent B is 5% water, 95% acetonitrile, 0.05% TFA, UV 220 nm.

Method J: XBridge Phenyl column (3.5 μm, 4.6×150 mm). Gradient elution (1.0 mL/min) from 10-100% Solvent B over 12 min and then 100% Solvent B for 3 min was used. Solvent A is 95% water, 5% acetonitrile, 0.05% TFA and Solvent B is 5% water, 95% acetonitrile, 0.05% TFA, UV 220 nm.

Method K: SunFire C18 column (3.5 μm, 4.6×150 mm). Gradient elution (1.0 mL/min) from 10-100% Solvent B over 25 min and then 100% Solvent B for 5 min was used. Solvent A is 95% water, 5% acetonitrile, 0.05% TFA and Solvent B is 5% water, 95% acetonitrile, 0.05% TFA, UV 220 nm.

Method L: XBridge Phenyl column (3.5 μm, 4.6×150 mm). Gradient elution (1.0 mL/min) from 10-100% Solvent B over 25 min and then 100% Solvent B for 5 min was used. Solvent A is 95% water, 5% acetonitrile, 0.05% TFA and Solvent B is 5% water, 95% acetonitrile, 0.05% TFA, UV 220 nm Method M: SunFire C18 column (3.5 μm, 4.6×150 mm). Gradient elution (1.0 mL/min) from 10-100% Solvent B over 18 min and then 100% Solvent B for 5 min was used. Solvent A is 95% water, 5% acetonitrile, 0.05% TFA and Solvent B is 5% water, 95% acetonitrile, 0.05% TFA, UV 220 nm.

Method N: XBridge Phenyl column (3.5 μm, 4.6×150 mm). Gradient elution (1.0 mL/min) from 10-100% Solvent B over 18 min and then 100% Solvent B for 5 min was used. Solvent A is 95% water, 5% acetonitrile, 0.05% TFA and Solvent B is 5% water, 95% acetonitrile, 0.05% TFA, UV 220 nm.

SFC and chiral purity methods

Method I: Chiralpak AD-H, 250×4.6 mm, 5.0-μm particles; % $CO_2$: 60%, % Co solvent: 40% {0.2% DEA IN IPA:ACN (1:1)}, Total Flow: 4.0 g/min, Back Pressure: 100 bars, Temperature: 25° C., UV: 218 nm.

Method II: Chiralpak OD-H, 250×4.6 mm, 5.0-μm particles; % $CO_2$: 60%, % Co solvent: 40% {0.2% DEA IN IPA:ACN (1:1)}, Total Flow: 4.0 g/min, Back Pressure: 104 bars, Temperature: 24.9° C., UV: 287 nm.

Method III: Chiralpak OJ-H, 250×4.6 mm, 5.0-μm particles; % $CO_2$: 60%, % Co— solvent: 30%(0.3% DEA in Methanol), Total Flow: 4.0 g/min, Back Pressure: 101 bars, Temperature: 23.6° C., UV: 272 nm.

Method IV: Chiralpak AS-H, 250×4.6 mm, 5.0-μm particles; % $CO_2$: 60%, % Co— solvent: 40%(0.3% DEA in Methanol), Total Flow: 4.0 g/min, Back Pressure: 102 bars, Temperature: 25.4° C., UV: 272 nm.

Method V: Chiralcel OJ-H, 250×4.6 mm, 5.0-μm particles; % $CO_2$: 60%, % Co-solvent: 40%(0.2% DEA in Methanol), Total Flow: 4.0 g/min, Back Pressure: 102 bars, Temperature: 24.6° C., UV: 272 nm.

Method VI: Luxcellulose-2, 250×4.6 mm, 5.0-μm particles; % $CO_2$: 60%, % Co-solvent: 35%(0.2% DEA in Methanol), Total Flow: 3.0 g/min, Back Pressure: 101 bars, Temperature: 23.6° C., UV: 260 nm.

Method VII: Chiralcel AS-H, 250×4.6 mm, 5.0-μm particles; % $CO_2$: 60%, % Co— solvent: 40%(0.2% DEA in Methanol), Total Flow: 4.0 g/min, Back Pressure: 101 bars, Temperature: 24.4° C., UV: 270 nm.

Method VIII: Chiralpak IC, 250×4.6 mm, 5.0-μm particles; % $CO_2$: 60%, % Co-solvent: 40%(0.2% DEA in Methanol), Total Flow: 4.0 g/min, Back Pressure: 101 bars, Temperature: 24.4° C., UV: 270 nm.

Method IX: COLUMN: chiralpakIF (250×4.6 mm), 5 micron, MOBILE PHASE: −0.2% DEA in ETHANOL, FLOW:1.0 ml/min.

Method X: COLUMN: LUX AMYLOSE 2 (250×4.6 mm), 5 micron, MOBILE PHASE: 0.2% DEA in n-HEXANE:ETHANOL:5:95, FLOW:1.0 ml/min.

Method XI: COLUMN: CHIRALCEL OD-H (250×4.6 mm), 5 micron, MOBILE PHASE: −0.2% DEA in n-HEXANE:ETHANOL:70:30, FLOW:1.0 ml/min.

Method XII: COLUMN: CHIRAL PAK ID 250×4.6 mm), 5 micron, MOBILE PHASE: −0.1% DEA in METHANOL, FLOW:1.0 ml/min.

NMR Employed in Characterization of Examples. $^1$H NMR spectra were obtained with Bruker or JEOL® Fourier transform spectrometers operating at frequencies as follows: $^1$H NMR: 400 MHz (Bruker or JEOL) or 500 MHz (Bruker or JEOL®). $^{13}$C NMR: 100 MHz (Bruker or JEOL). Spectra data are reported in the format: chemical shift (multiplicity, coupling constants, number of hydrogens). Chemical shifts are specified in ppm downfield of a tetramethylsilane internal standard (δ units, tetramethylsilane=0 ppm) and/or referenced to solvent peaks, which in $^1$H NMR spectra appear at 2.49 ppm for $CD_2HSOCD_3$, 3.30 ppm for $CD_2HOD$, 1.94 for $CD_3CN$, and 7.24 ppm for $CHCl_3$, and which in $^{13}$C NMR spectra appear at 39.7 ppm for $CD_3SOCD_3$, 49.0 ppm for $CD_3OD$, and 77.0 ppm for $CDCl_3$. All $^{13}$C NMR spectra were proton decoupled.

Example 1: (R)—N-((1-(4-(2-Oxo-3-(3-(6-(trifluoromethyl)pyridin-3-yl)ureido)piperidin-1-yl)phenyl)cyclobutyl)methyl)methanesulfonamide

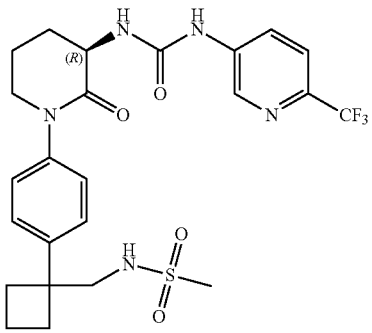

Example 1A: 1-(4-Bromophenyl)cyclobutane-1-carbonitrile

A solution of 2-(4-bromophenyl)acetonitrile (5.0 g, 26 mmol) in DMF (5 mL) was added via cannula to a stirred suspension of NaH (2.3 g, 59 mmol) in DMF (45 mL) under argon atmosphere at 0° C. After 20 min, 1,3-dibromopropane (2.9 mL, 28 mmol) was added to the reaction mixture and the mixture was gradually brought to room temperature. After 16 hours, the reaction mixture was quenched with water (50 mL) and extracted with 50% EtOAc-pet ether (3×50 mL). The combined organic extracts were washed with brine (3×30 mL), dried over $Na_2SO_4$ and concentrated under reduced pressure. The crude residue was purified by silica gel column chromatography (5% EtOAc-Pet ether) to afford Example 1A as a colorless liquid. $^1$H NMR (400 MHz, $CDCl_3$): δ 7.59-7.50 (m, 2H), 7.31-7.23 (m, 2H), 2.88-2.78 (m, 2H), 2.64-2.58 (m, 2H), 2.45-2.36 (m, 1H), 2.14-2.02 (m, 1H).

Example 1B: tert-Butyl (1-(4-(1-cyanocyclobutyl)phenyl)-2-oxopiperidin-3-yl)carbamate Example 1A (1.1 g, 4.7 mmol) and $Cs_2CO_3$ (2.3 g, 7.0 mmol) were added to a stirred solution of tert-butyl (2-oxopiperidin-3-yl)carbamate (1 g, 4.7 mmol) in 1,4-dioxane (10 mL). The reaction mixture was purged with nitrogen for 5 min and then charged with Xantphos (0.27 g, 0.47 mmol) and $Pd_2(dba)_3$ (0.21 g, 0.23 mmol). The reaction mixture was again purged with nitrogen for 3 min and heated at 110° C. for 16 hours. The reaction mixture was cooled, filtered through a Celite pad and the filtrate was concentrated under reduced pressure. The residue was purified using column chromatography (EtOAc-Pet ether) to afford Example 1B (1.0 g, 2.7 mmol, 58% yield) as a brown solid. MS(ESI) m/z: 370.6 (M+H)+; $^1$H NMR (400 MHz, $CDCl_3$) (δ 7.51-7.38 (m, 2H), 7.33-7.26 (m, 2H), 5.46 (br. s., 1H), 4.35-4.22 (m, 1H), 3.74-3.68 (m, 2H), 2.89-2.78 (m, 2H), 2.68-2.56 (m, 3H), 2.48-2.35 (m, 1H), 2.12-1.96 (m, 3H), 1.78-1.68 (m, 1H), 1.42 (s, 9H).

Example 1C: tert-Butyl (1-(4-(1-(aminomethyl)cyclobutyl)phenyl)-2-oxopiperidin-3-yl)carbamate To a stirred solution of Example 1B (300 mg, 0.812 mmol) in MeOH (10 mL), was added Raney nickel (70 mg, 0.81 mmol). The resulting mixture was stirred for overnight under $H_2$, filtered through syringe filter and concentrated under reduced pressure. The crude residue was triturated with hexane (2×10 mL) to afford Example 1C (150 mg, 0.40 mmol, 50% yield) as a brown solid. MS(ESI) m/z: 374.3 (M+H)+.

Example 1D: tert-Butyl (1-(4-(1-(methylsulfonamidomethyl)cyclobutyl)phenyl)-2-oxopiperidin-3-yl)carbamate To a stirred solution of Example 1C (400 mg, 1.1 mmol) in DCM (5 mL) at 0° C., were added TEA (0.30 mL, 2.1 mmol) and mesylchloride (0.10 mL, 1.3 mmol). The reaction mixture was gradually warmed to room temperature and stirred for 1 hour. The reaction mixture was quenched with water (10 mL) and extracted with DCM (2×20 mL). The combined organic layers were washed with brine (20 mL), dried over $Na_2SO_4$ and concentrated under reduced pressure. The crude residue was triturated with pet ether (20 mL) to afford Example 1D (440 mg, 0.97 mmol, 91% yield) as a brown solid. MS(ESI) m/z: 452.2 (M+H)+.

Example 1E: N-((1-(4-(3-Amino-2-oxopiperidin-1-yl)phenyl)cyclobutyl)methyl)methanesulfonamide hydrochloride To an ice cooled solution of Example 1D (200 mg, 0.44 mmol) in 1,4-dioxane (2 mL), was added 4 N HCl in 1,4-dioxane (2.2 ml, 8.9 mmol), and the mixture was stirred at rt for two hours. The solvent was evaporated and dried under reduced pressure to obtain a gummy solid. The solid was triturated with diethyl ether (2×20 mL) and dried to afford Example 1E (150 mg, 0.43 mmol, 96% yield) as a brown solid. MS(ESI) m/z: 352.2 (M+H)+.

Example 1: (R)—N-((1-(4-(2-Oxo-3-(3-(6-(trifluoromethyl)pyridin-3-yl)ureido)piperidin-1-yl)phenyl)cyclobutyl)methyl)methanesulfonamide To an ice cooled suspension of Example 1E (75 mg, 0.19 mmol) in 1,2-dichloroethane (2 mL) were added DIPEA (0.068 mL, 0.39 mmol) and phenyl (6-(trifluoromethyl)pyridin-3-yl)carbamate (55 mg, 0.19 mmol). The resulting solution was heated at 50° C. for 15 hours. The reaction mixture was concentrated under reduced pressure and the residue was purified by column chromatography followed by chiral HPLC to afford Example 1 (24 mg, 0.044 mmol, 23% yield) as a white solid. RT=1.58 min, 99% (Method F); MS(ESI) m/z: 540.2 (M+H)+; $^1$H NMR (400 MHz, DMSO-d6): δ9.62 (s, 1H), 8.69 (d, J=2.2 Hz, 1H), 8.14 (d, J=8.6 Hz, 1H), 7.76 (d, J=8.6 Hz, 1H), 7.24 (d, J=8.3 Hz, 2H), 7.17 (d, J=8.3 Hz, 2H), 7.01 (d, J=6.6 Hz, 1H), 6.97-6.86 (m, 1H), 4.36-4.29 (m, 1H), 3.65 (d, J=6.8 Hz, 2H), 3.20 (d, J=6.6 Hz, 2H), 2.61 (s, 3H), 2.32-2.18 (m, 5H), 2.03-1.91 (m, 3H), 1.86-1.69 (m, 2H).

Additional examples of compounds of this invention shown in Table 1 below were prepared using combinations of the procedures described in Example 1 or modifications thereof known to one skilled in the art of organic synthesis.

TABLE 1

| Ex | Structure and Name | LCMS (M + H)+ | HPLC Method, RT (min.) & Purity | ¹H NMR |
|---|---|---|---|---|
| 2 | 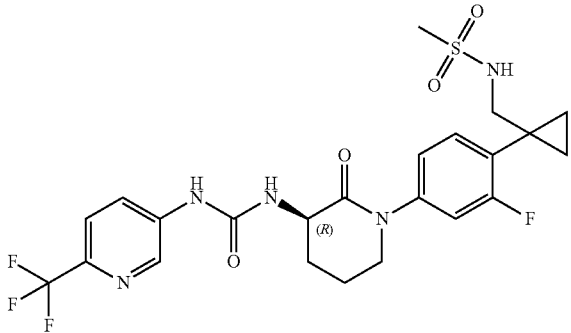<br>(R)-N-((1-(2-fluoro-4-(2-oxo-3-(3-(6-(trifluoromethyl)pyridin-3-yl)ureido)piperidin-1-yl)phenyl)cyclopropyl)methyl)methanesulfonamide | 544.2 | Method F, RT = 1.492 min, 100% | ¹H NMR (400 MHz, DMSO-d6): δ 9.43 (s, 1H), 8.67 (d, J = 2.2 Hz, 1H), 8.12 (d, J = 10.5 Hz, 1H), 7.76 (d, J = 8.6 Hz, 1H), 7.35 (t, J = 8.3 Hz, 1H), 7.15 (d, J = 11.7 Hz, 1H), 7.12-6.99 (m, 2H), 6.82 (d, J = 6.4 Hz, 1H), 4.37-4.27 (m, 1H), 3.73-3.62 (m, 2H), 3.10 (d, J = 6.4 Hz, 2H), 2.69 (s, 3H), 2.28-2.20 (m, 1H), 2.03-1.91 (m, 2H), 1.86-1.77 (m, 1H), 0.96-0.82 (m, 2H), 0.79-0.68 (m, 2H) |
| 3 | 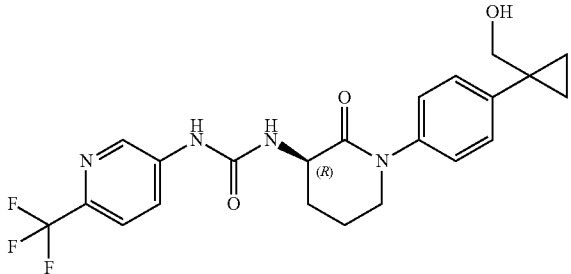<br>(R)-1-(1-(4-(1-(hydroxymethyl)cyclopropyl)phenyl)-2-oxopiperidin-3-yl)-3-(6-(trifluoromethyl)pyridin-3-yl)urea | 449.2 | Method F, RT = 1.465 min, 100% | ¹H NMR (400 MHz, DMSO-d6): δ 9.56 (s, 1H), 8.69 (d, J = 2.7 Hz, 1H), 8.15 (d, J = 8.6 Hz, 1H), 7.77 (d, J = 8.8 Hz, 1H), 7.31 (d, J = 8.6 Hz, 2H), 7.19 (d, J = 8.6 Hz, 2H), 6.95 (d, J = 6.6 Hz, 1H), 4.36-4.30 (m, 1H), 3.75-3.55 (m, 4H), 2.81 (m, 1H), 2.29-2.21 (m, 1H), 1.95-1.90 (m, 2H), 1.75-1.65 (m, 1H), 0.86-0.79 (m, 2H), 0.76-0.68 (m, 2H). |
| 4 | 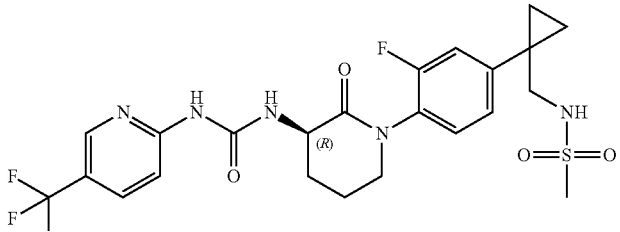<br>(R)-N-((1-(3-fluoro-4-(2-oxo-3-(3-(5-(trifluoromethyl)pyridin-2-yl)ureido)piperidin-1-yl)phenyl)cyclopropyl)methyl)methanesulfonamide | 544.2 | Method F, RT = 1.684 min, 100% | ¹H NMR (400 MHz, DMSO-d6): δ 9.77 (s, 1H), 8.56 (s, 1H), 8.10 (d, J = 6.4 Hz, 1H), 8.06 (dd, J = 9.0, 2.4 Hz, 1H), 7.73 (d, J = 9.0 Hz, 1H), 7.31 (t, J = 8.3 Hz, 1H), 7.23 (dd, J = 11.9, 1.8 Hz, 1H), 7.18 (dd, J = 8.3, 2.1 Hz, 1H), 7.10 (t, J = 6.1 Hz, 1H), 4.49-4.35 (m, 1H), 3.65-3.56 (m, 2H), 3.13 (d, J = 6.1 Hz, 2H), 2.78 (s, 3H), 2.35-2.27 (m, 1H), 2.07-1.93 (m, 2H), 1.88-1.74 (m, 1H), 0.99-0.92 (m, 2H), 0.90-0.78 (m, 2H). |

TABLE 1-continued

| Ex | Structure and Name | LCMS (M + H)+ | HPLC Method, RT (min.) & Purity | ¹H NMR |
|---|---|---|---|---|
| 5 | 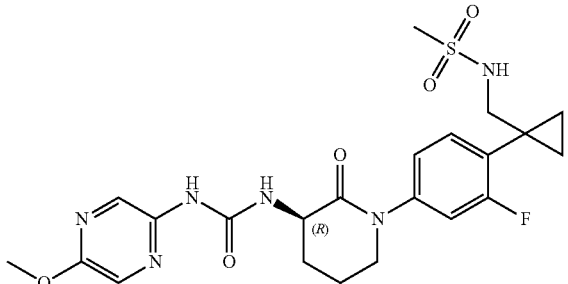<br>(R)-N-((1-(2-fluoro-4-(3-(3-(5-methoxypyrazin-2-yl)ureido)-2-oxopiperidin-1-yl)phenyl)cyclopropyl)methyl)methanesulfonamide | 507.2 | Method F, RT = 1.288 min, 100% | ¹H NMR (400 MHz, DMSO-d6): δ 9.23 (s, 1H), 8.53 (s, 1H), 7.95 (s, 1H), 7.40-7.28 (m, 2H), 7.16 (s, 1H), 7.12-6.98 (m, 2H), 4.39-4.26 (m, 1H), 3.84 (s, 3H), 3.72-3.62 (m, 2H), 3.10 (d, J = 6.1 Hz, 2H), 2.68 (s, 3H), 2.32-2.25 (m, 1H), 2.02-1.89 (m, 2H), 1.80-1.73 (m, 1H), 0.92-0.84 (m, 2H), 0.82-0.60 (m, 2H). |
| 6 | 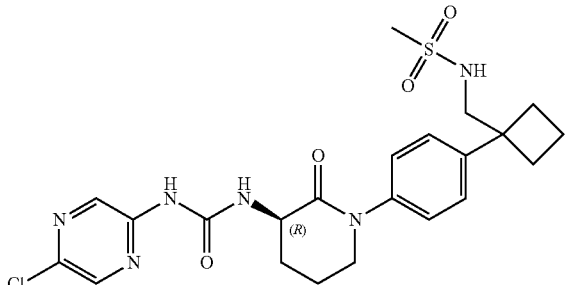<br>(R)-N-((1-(4-(3-(3-(5-chloropyrazin-2-yl)ureido)-2-oxopiperidin-1-yl)phenyl)cyclobutyl)methyl)methanesulfonamide | 507.2 | Method F, RT = 1.451 min, 100% | ¹H NMR (400 MHz, DMSO-d6): δ 9.75 (s, 1H), 8.85 (s, 1H), 8.37 (s, 1H), 7.48 (d, J = 6.8 Hz, 1H), 7.25 (d, J = 8.1 Hz, 2H), 7.14 (d, J = 8.1 Hz, 2H), 6.93 (t, J = 6.1 Hz, 1H), 4.41-4.31 (m, 1H), 3.72-3.62 (m, 2H), 3.20 (d, J = 6.1 Hz, 2H), 2.62 (s, 3H), 2.36-2.18 (m, 5H), 2.03-1.92 (m, 3H), 1.85-1.70 (m, 2H). |
| 7 | 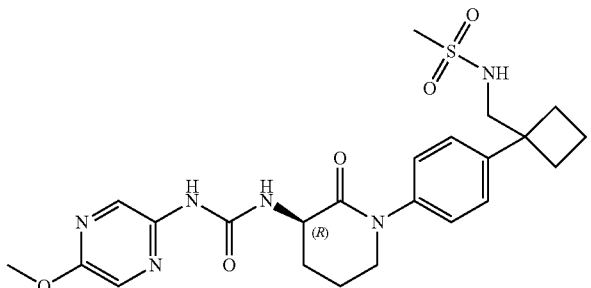<br>(R)-N-((1-(4-(3-(3-(5-methoxypyrazin-2-yl)ureido)-2-oxopiperidin-1-yl)phenyl)cyclobutyl)methyl)methanesulfonamide | 503.2 | Method F, RT = 1.379 min, 100% | ¹H NMR (400 MHz, DMSO-d6): δ 9.23 (s, 1H), 8.57 (s, 1H), 7.96 (s, 1H), 7.29 (d, J = 6.8 Hz, 1H), 7.24 (d, J = 8.3 Hz, 2H), 7.17 (d, J = 8.3 Hz, 2H), 6.93 (t, J = 6.8 Hz, 1H), 4.41-4.29 (m, 1H), 3.85 (s, 3H), 3.72-3.58 (m, 2H), 3.20 (d, J = 6.8 Hz, 2H), 2.61 (s, 3H), 2.37-2.15 (m, 5H), 2.07-1.89 (m, 3H), 1.85-1.70 (m, 2H) |

TABLE 1-continued

| Ex | Structure and Name | LCMS (M + H)+ | HPLC Method, RT (min.) & Purity | ¹H NMR |
|---|---|---|---|---|
| 8 | 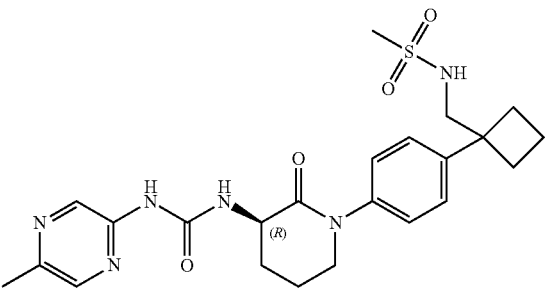<br>(R)-N-((1-(4-(3-(3-(5-methylpyrazin-2-yl)ureido)-2-oxopiperidin-1-yl)phenyl)cyclobutyl)methyl)methanesulfonamide | 487.3 | Method F, RT = 1.306 min, 100% | ¹H NMR (400 MHz, DMSO-d6): δ 9.44 (s, 1H), 8.78 (s, 1H), 8.10 (s, 1H), 7.77 (br. s., 1H), 7.25 (d, J = 8.3 Hz, 2H), 7.15 (d, J = 7.8 Hz, 2H), 6.93 (t, J = 6.6 Hz, 1H), 4.43-4.33 (m, 1H), 3.71-3.61 (m, 2H), 3.22 (d, J = 6.6 Hz, 2H), 2.62 (s, 3H), 2.38 (s, 3H), 2.36-2.17 (m, 5H), 2.02-1.93 (m., 3H), 1.81-1.74 (m., 2H) |
| 9 | 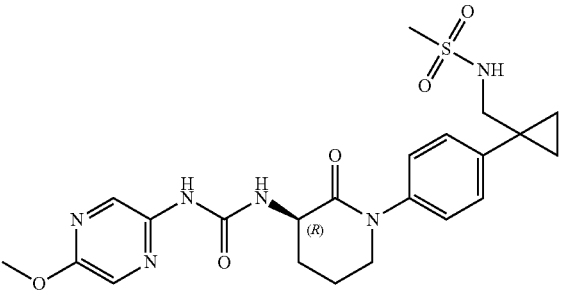<br>(R)-N-((1-(4-(3-(3-(5-methoxypyrazin-2-yl)ureido)-2-oxopiperidin-1-yl)phenyl)cyclopropyl)methyl)methanesulfonamide | 489.3 | Method F, RT = 1.234 min, 100% | ¹H NMR (400 MHz, DMSO-d6): δ 9.22 (s, 1H), 8.55 (s, 1H), 7.95 (s, 1H), 7.37-7.26 (m, 3H), 7.21 (d, J = 8.6 Hz, 2H), 7.03 (t, J = 6.1 Hz, 1H), 4.41-4.26 (m, 1H), 3.84 (s, 3H), 3.71-3.57 (m, 2H), 3.14 (d, J = 6.1 Hz, 2H), 2.71 (s, 3H), 2.30-2.22 (m, 1H), 2.03-1.90 (m, 2H), 1.83-1.66 (m, 1H), 0.93-0.83 (m, 2H), 0.83-0.69 (m, 2H). |
| 10 | 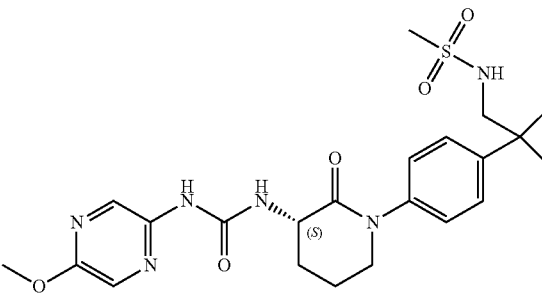<br>(S)-N-((1-(4-(3-(3-(5-methoxypyrazin-2-yl)ureido)-2-oxopiperidin-1-yl)phenyl)cyclobutyl)methyl)methanesulfonamide | 503.2 | Method F, RT = 1.379 min, 100% | ¹H NMR (400 MHz, DMSO-d6): δ 9.23 (s, 1H), 8.57 (s, 1H), 7.96 (s, 1H), 7.29 (d, J = 6.8 Hz, 1H), 7.24 (d, J = 8.3 Hz, 2H), 7.17 (d, J = 8.3 Hz, 2H), 6.93 (t, J = 6.8 Hz, 1H), 4.41-4.29 (m, 1H), 3.85 (s, 3H), 3.72-3.58 (m, 2H), 3.20 (d, J = 6.8 Hz, 2H), 2.61 (s, 3H), 2.37-2.15 (m, 5H), 2.07-1.89 (m, 3H), 1.85-1.70 (m, 2H). |

TABLE 1-continued

| Ex | Structure and Name | LCMS (M + H)+ | HPLC Method, RT (min.) & Purity | $^1$H NMR |
|---|---|---|---|---|
| 11 | 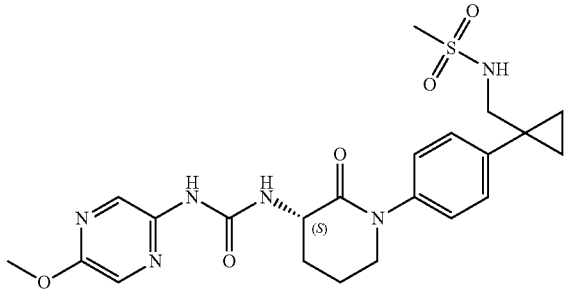<br>(S)-N-((1-(4-(3-(3-(5-methoxypyrazin-2-yl)ureido)-2-oxopiperidin-1-yl)phenyl)cyclopropyl)methyl)methanesulfonamide | 489.3 | Method F, RT = 1.233 min, 100% | $^1$H NMR (400 MHz, DMSO-d6): δ 9.22 (s, 1H), 8.55 (s, 1H), 7.95 (s, 1H), 7.37-7.26 (m, 3H), 7.21 (d, J = 8.6 Hz, 2H), 7.03 (t, J = 6.1 Hz, 1H), 4.41-4.26 (m, 1H), 3.84 (s, 3H), 3.71-3.57 (m, 2H), 3.14 (d, J = 6.1 Hz, 2H), 2.71 (s, 3H), 2.30-2.22 (m, 1H), 2.03-1.90 (m, 2H), 1.83-1.66 (m, 1H), 0.93-0.83 (m, 2H), 0.83-0.69 (m, 2H) |
| 12 | 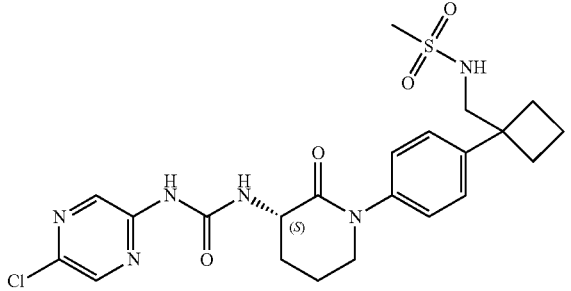<br>(S)-N-((1-(4-(3-(3-(5-chloropyrazin-2-yl)ureido)-2-oxopiperidin-1-yl)phenyl)cyclobutyl)methyl)methanesulfonamide | 507.2 | Method F, RT = 1.451 min, 100% | $^1$H NMR (400 MHz, DMSO-d6): δ 9.75 (s, 1H), 8.85 (s, 1H), 8.37 (s, 1H), 7.48 (d, J = 6.8 Hz, 1H), 7.25 (d, J = 8.1 Hz, 2H), 7.14 (d, J = 8.1 Hz, 2H), 6.93 (t, J = 6.8 Hz, 1H), 4.41-4.31 (m, 1H), 3.72-3.62 (m, 2H), 3.20 (d, J = 6.8 Hz, 2H), 2.62 (s, 3H), 2.36-2.18 (m, 5H), 2.03-1.92 (m, 3H), 1.85-1.70 (m, 2H). |
| 13 | 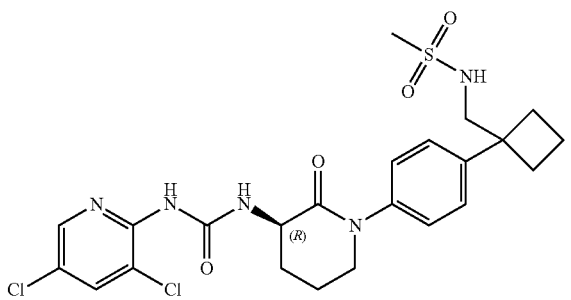<br>(R)-N-((1-(4-(3-(3-(3,5-dichloropyridin-2-yl)ureido)-2-oxopiperidin-1-yl)phenyl)cyclobutyl)methyl)methanesulfonamide | 540.2 | Method F, RT = 1.688 min, 98.4% | $^1$H NMR (400 MHz, DMSO-d6): δ 8.95 (d, J = 5.4 Hz, 1H), 8.55 (s, 1H), 8.27 (d, J = 2.2 Hz, 1H), 8.17 (d, J = 2.0 Hz, 1H), 7.24 (d, J = 8.3 Hz, 2H), 7.16 (d, J = 8.6 Hz, 2H), 6.90 (t, J = 6.8 Hz, 1H), 4.44-4.36 (m, 1H), 3.69-3.59 (m, 2H), 3.20 (d, J = 6.8 Hz, 2H), 2.62 (s, 3H), 2.38-2.30 (m, 1H), 2.29-2.22 (m, 4H), 2.03-1.93 (m, 3H), 1.90-1.82 (m, 1H), 1.80-1.73 (m, 1H). |

TABLE 1-continued

| Ex | Structure and Name | LCMS (M + H)+ | HPLC Method, RT (min.) & Purity | ¹H NMR |
|---|---|---|---|---|
| 14 | 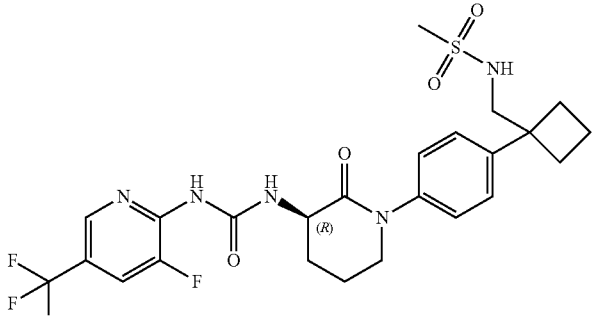<br>(R)-N-((1-(4-(3-(3-(3-fluoro-5-(trifluoromethyl)pyridin-2-yl)ureido)-2-oxopiperidin-1-yl)phenyl)cyclobutyl)methyl)methanesulfonamide | 558.2 | Method F, RT = 1.693 min, 98.8% | ¹H NMR (400 MHz, DMSO-d6): δ 9.73 (s, 1H), 9.28 (d, J = 6.4 Hz, 1H), 8.43 (s, 1H), 8.16 (d, J = 10.3 Hz, 1H), 7.25 (d, J = 8.3 Hz, 2H), 7.16 (d, J = 8.3 Hz, 2H), 6.91 (t, J = 6.6 Hz, 1H), 4.50-4.38 (m, 1H), 3.71-3.62 (m, 2H), 3.18 (d, J = 6.6 Hz, 2H), 2.63 (s, 3H), 2.40-2.30 (m, 1H), 2.31-2.15 (m, 4H), 2.03-1.95 (m, 3H), 1.90-1.71 (m, 2H). |
| 15 | 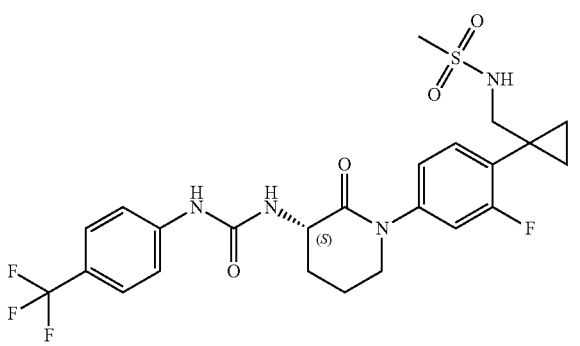<br>(S)-N-((1-(2-fluoro-4-(2-oxo-3-(3-(4-(trifluoromethyl)phenyl)ureido)piperidin-1-yl)phenyl)cyclopropyl)methyl)methanesulfonamide | 543.2 | Method F, RT = 1.704 min, 96.1% | ¹H NMR (400 MHz, DMSO-d6): δ 9.18 (s, 1H), 7.57 (s, 4H), 7.34 (t, J = 8.4 Hz, 1H), 7.14 (d, J = 12.0 Hz, 1H), 7.12-7.01 (m, 2H), 6.65 (d, J = 6.8 Hz, 1H), 4.35-4.21 (m, 1H), 3.74-3.68 (m, 2H), 3.10 (d, J = 6.6 Hz, 2H), 2.72-2.65 (m, 3H), 2.28-2.22 (m, 1H), , 2.01-1.90 (m, 2H), 1.84-1.74 (m, 1H), 0.93-0.80 (m, 2H), 0.79-150.68 (m, 2H). |
| 16 | 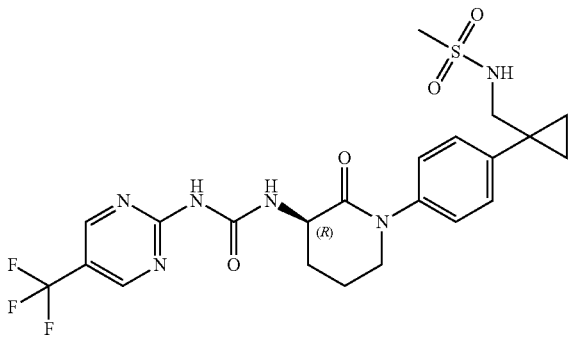<br>(R)-N-((1-(4-(2-oxo-3-(3-(5-(trifluoromethyl)pyrimidin-2-yl)ureido)piperidin-1-yl)phenyl)cyclopropyl)methyl)methanesulfonamide | 527.2 | Method F, RT = 1.414 min, 100% | ¹H NMR (400 MHz, DMSO-d6,): δ 10.45 (s, 1H), 9.35 (d, J = 6.4 Hz, 1H), 8.97 (s, 2H), 7.35 (d, J = 8.3 Hz, 2H), 7.21 (d, J = 8.3 Hz, 2H), 7.04 (t, J = 6.2 Hz, 1H), 4.45 (dt, J = 11.9, 6.1 Hz, 1H), 3.75-3.60 (m, 2H), 3.13 (d, J = 6.2 Hz, 2H), 2.73 (s, 3H), 2.40-2.36 (m, 1H), 2.00-1.98 (m, 2H), 1.89-1.73 (m, 1H), 0.92-0.87 (m, 2H), 0.83-0.75 (m, 2H). |

TABLE 1-continued

| Ex | Structure and Name | LCMS (M + H)+ | HPLC Method, RT (min.) & Purity | ¹H NMR |
|---|---|---|---|---|
| 17 | 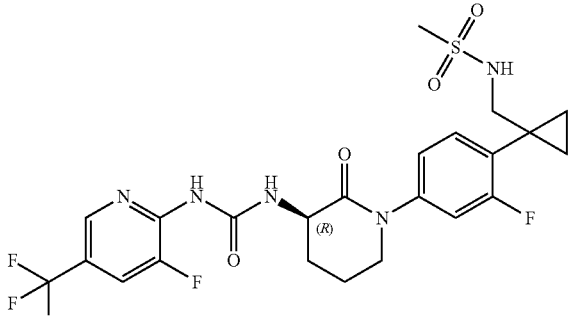<br>(R)-N-((1-(2-fluoro-4-(3-(3-(3-fluoro-5-(trifluoromethyl)pyridin-2-yl)ureido)-2-oxopiperidin-1-yl)phenyl)cyclopropyl)methyl)methanesulfonamide | 562.2 | Method F, RT = 1.612 min, 97.9% | ¹H NMR (400 MHz, DMSO-d6): δ 9.79 (s, 1H), 9.28 (d, J = 6.1 Hz, 1H), 8.44 (s, 1H), 8.19 (d, J = 10.0 Hz, 1H), 7.36 (t, J = 8.4 Hz, 1H), 7.18 (dd, J = 11.9, 1.8 Hz, 1H), 7.14-6.95 (m, 2H), 4.55-4.36 (m, 1H), 3.76-3.62 (m, 2H), 3.11 (d, J = 6.4 Hz, 2H), 2.70 (s, 3H), 2.40-2.34 (m, 1H), 2.05-1.93 (m, 2H), 1.88-1.74 (m, 1H), 0.93-0.87 (m, 2H), 0.78-0.72 (m, 2H). |
| 18 | 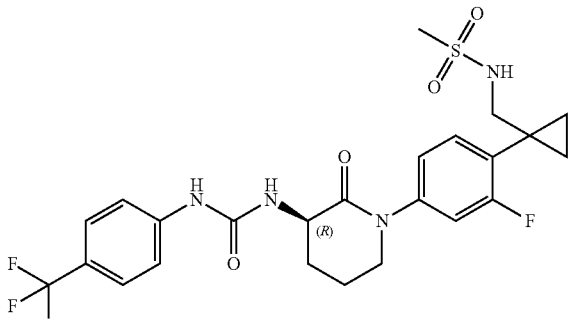<br>(R)-N-((1-(2-fluoro-4-(3-(3-oxo-3-(3-(4-(trifluoromethyl)phenyl)ureido)piperidin-1-yl)phenyl)cyclopropyl)methyl)methanesulfonamide | 543.2 | Method F, RT = 1.696 min, 94.4.1% | ¹H NMR (400 MHz, DMSO-d6): δ 9.18 (s, 1H), 7.61-7.54 (m, 4H), 7.34 (t, J = 8.4 Hz, 1H), 7.14 (d, J = 12.0 Hz, 1H), 7.12-7.01 (m, 2H), 6.65 (d, J = 6.8 Hz, 1H), 4.35-4.21 (m, 1H), 3.74-3.68 (m, 2H), 3.10 (d, J = 6.6 Hz, 2H), 2.72-2.65 (m, 3H), 2.28-2.22 (m, 1H), 2.01-1.90 (m, 2H), 1.84-1.74 (m, 1H), 0.93-0.80 (m, 2H), 0.79-0.68 (m, 2H). |
| 19 | 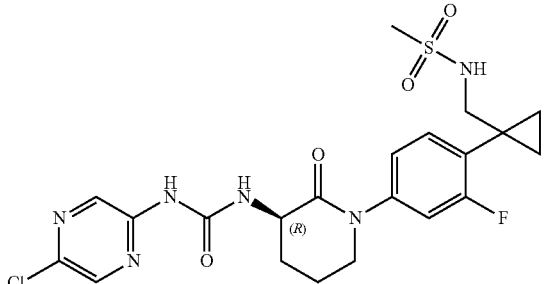<br>(R)-N-((1-(4-(3-(3-(5-chloropyrazin-2-yl)ureido)-2-oxopiperidin-1-yl)-2-fluorophenyl)cyclopropyl)methyl)methanesulfonamide | 511.2 | Method F, RT = 1.37 min, 100% | ¹H NMR (400 MHz, DMSO-d6): δ 9.75 (s, 1H), 8.82 (s, 1H), 8.36 (s, 1H), 7.49 (d, J = 6.8 Hz, 1H), 7.35 (t, J = 8.4 Hz, 1H), 7.15 (d, J = 12.01 Hz, 1H), 7.12-6.96 (m, 2H), 4.45-4.29 (m, 1H), 3.74-3.59 (m, 2H), 3.10 (d, J = 6.4 Hz, 2H), 2.69 (s, 3H), 2.32-2.26 (m, 1H), 2.03-1.91 (m, 2H), 1.87-1.73 (m, 1H), 0.98-0.84 (m, 2H), 0.80-0.64 (m, 2H). |

TABLE 1-continued

| Ex | Structure and Name | LCMS (M + H)+ | HPLC Method, RT (min.) & Purity | ¹H NMR |
|---|---|---|---|---|
| 20 | 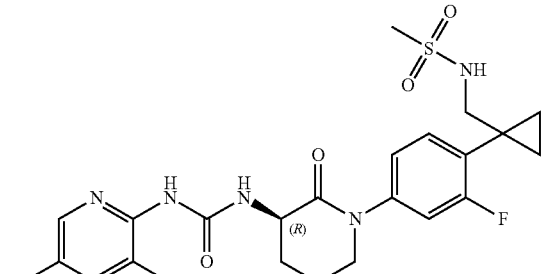<br>(R)-N-((1-(4-(3-(3-(5-chloro-3-fluoropyridin-2-yl)ureido)-2-oxopiperidin-1-yl)-2-fluorophenyl)cyclopropyl)methyl)methanesulfonamide | 528.2 | Method F, RT = 1.492 min, 99.23% | ¹H NMR (400 MHz, DMSO-d6): δ 9.35 (s, 1H), 8.87 (br. s., 1H), 8.13 (s, 1H), 7.98 (d, J = 10.3 Hz, 1H), 7.35 (t, J = 8.4 Hz, 1H), 7.16 (d, J = 12.0 Hz, 1H), 7.12-6.97 (m, 2H), 4.48-4.34 (m, 1H), 3.75-3.61 (m, 2H), 3.10 (d, J = 6.4 Hz, 2H), 2.69 (s, 3H), 2.36-2.28 (m, 1H), 1.96 (d, J = 6.1 Hz, 2H), 1.89-1.72 (m, 1H), 0.92-0.86 (m, 2H), 0.78-0.72 (m, 2H). |
| 21 | 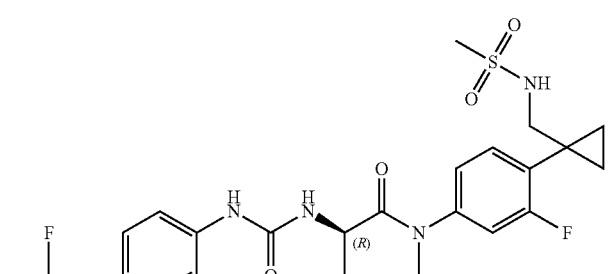<br>(R)-N-((1-(4-(3-(3-(6-(difluoromethoxy)pyridin-3-yl)ureido)-2-oxopiperidin-1-yl)-2-fluorophenyl)cyclopropyl)methyl)methanesulfonamide | 542.2 | Method F, RT = 1.448 min, 99.18% | ¹H NMR (400 MHz, DMSO-d6): δ 8.97 (s, 1H), 8.25 (d, J = 2.7 Hz, 1H), 7.94 (dd, J = 8.8, 2.7 Hz, 1H), 7.56 (s, 1H), 7.47-7.25 (m, 1H), 7.15 (d, J = 12.0 Hz, 1H), 7.12-7.03 (m, 2H), 7.00 (d, J = 9.0 Hz, 1H), 6.62 (d, J = 6.8 Hz, 1H), 4.39-4.25 (m, 1H), 3.75-3.59 (m, 2H) 3.10 (d, J = 6.4 Hz, 2H), 2.69 (s, 3H), 2.28-2.20 (m, 1H), 2.02-1.92 (m, 2H), 1.85-1.71 (m, 1H), 0.92-0.85 (m, 2H), 0.78-0.72 (m, 2H). |
| 22 | 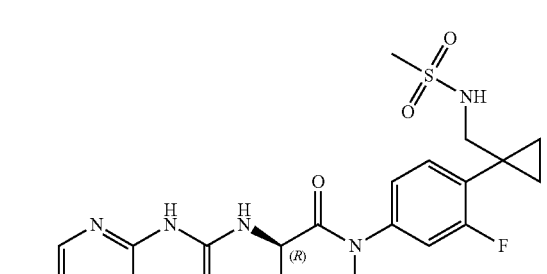<br>(R)-N-((1-(4-(3-(3-(3,5-dichloropyridin-2-yl)ureido)-2-oxopiperidin-1-yl)-2-fluorophenyl)cyclopropyl)methyl)methanesulfonamide | 544.2 | Method F, RT = 1.611 min, 99.4% | ¹H NMR (400 MHz, DMSO-d6): δ 8.97 (d, J = 6.4 Hz, 1H), 8.56 (s, 1H), 8.27 (d, J = 2.2 Hz, 1H), 8.17 (d, J = 2.2 Hz, 1H), 7.35 (t, J = 8.4 Hz, 1H), 7.16 (d, J = 11.7 Hz, 1H), 7.12-6.98 (m, 2H), 4.48-4.34 (m, 1H), 3.74-3.62 (m, 2H), 3.10 (d, J = 6.4 Hz, 2H), 2.69 (s, 3H), 2.36-2.28 (m, 1H), 2.02-1.90 (m, 2H), 1.87-1.76 (m, 1H), 0.92-0.85 (m, 2H), 0.79-0.73 (m, 2H). |

TABLE 1-continued

| Ex | Structure and Name | LCMS (M + H)+ | HPLC Method, RT (min.) & Purity | ¹H NMR |
|---|---|---|---|---|
| 23 | 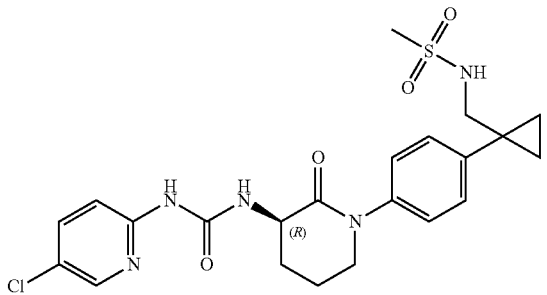<br>(R)-N-((1-(4-(3-(3-(5-chloropyridin-2-yl)ureido)-2-oxopiperidin-1-yl)phenyl)cyclopropyl)methyl)methanesulfonamide | 492.2 | Method F, RT = 1.433 min, 100% | ¹H NMR (400 MHz, DMSO-d6): δ 9.45 (s, 1H), 8.20 (d, J = 2.7 Hz, 1H), 7.97 (br. s., 1H), 7.78 (dd, J = 9.0, 2.7 Hz, 1H), 7.57 (d, J = 8.8 Hz, 1H), 7.35 (d, J = 8.3 Hz, 2H), 7.20 (d, J = 8.3 Hz, 2H), 7.04 (t, J = 6.4 Hz, 1H), 4.44-4.27 (m, 1H), 3.72-3.58 (m, 2H), 3.13 (d, J = 6.4 Hz, 2H), 2.77 (s, 3H), 2.33-2.26 (m, 1H), 2.05-1.89 (m, 2H), 1.84-1.70 (m, 1H), 0.95-0.84 (m, 2H), 0.83-0.67 (m, 2H). |
| 24 | 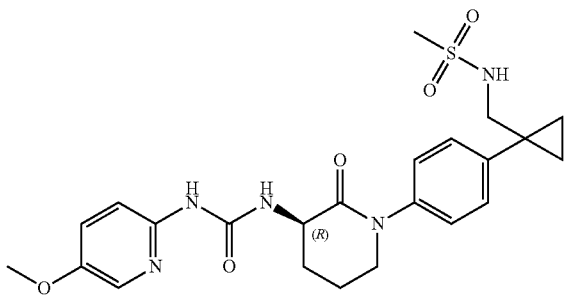<br>(R)-N-((1-(4-(3-(3-(5-methoxypyridin-2-yl)ureido)-2-oxopiperidin-1-yl)phenyl)cyclopropyl)methyl)methanesulfonamide | 488.2 | Method F, RT = 1.281 min, 100% | ¹H NMR (400 MHz, DMSO-d6): δ 9.13 (s, 1H), 8.24 (br. s., 1H), 7.88 (t, J = 1.8 Hz, 1H), 7.44-7.28 (m, 4H), 7.28-7.18 (m, 2H), 7.04 (t, J = 6.4 Hz, 1H), 4.43-4.30 (m, 1H), 3.76 (s, 3H), 3.71-3.57 (m, 2H), 3.13 (d, J = 6.4 Hz, 2H), 2.72 (s, 3H), 2.34-2.25 (m, 1H), 2.02-1.90 (m, 2H), 1.82-1.71 (m, 1H), 0.94-0.85 (m, 2H), 0.83-0.72 (m, 2H). |
| 25 | 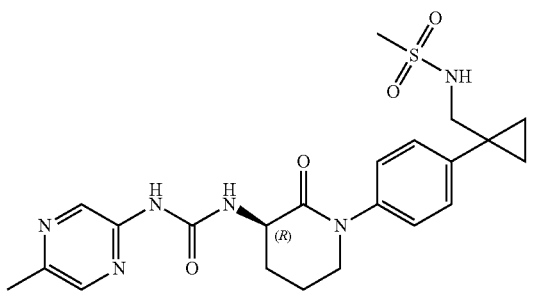<br>(R)-N-((1-(4-(3-(3-(5-methylpyrazin-2-yl)ureido)-2-oxopiperidin-1-yl)phenyl)cyclopropyl)methyl)methanesulfonamide | 473.3 | Method F, RT = 1.145 min, 100% | ¹H NMR (DMSO-d6, 400 MHz): δ 9.43 (s, 1H), 8.77 (s, 1H), 8.10 (s, 1H), 7.78 (d, J = 5.9 Hz, 1H), 7.33 (d, J = 8.3 Hz, 2H), 7.22 (d, J = 8.3 Hz, 2H), 7.04 (t, J = 6.4 Hz, 1H), 4.41-4.32 (m, 1H), 3.70-3.63 (m, 2H), 3.13 (d, J = 6.4 Hz, 2H), 2.75 (s, 3H), 2.38 (s, 3H), 2.33-2.28 (m, 1H), 2.03-1.90 (m, 2H), 1.84-1.70 (m, 1H), 0.94-0.84 (m, 2H), 0.83-0.70 (m, 2H). |

TABLE 1-continued

| Ex | Structure and Name | LCMS (M + H)+ | HPLC Method, RT (min.) & Purity | ¹H NMR |
|---|---|---|---|---|
| 26 | 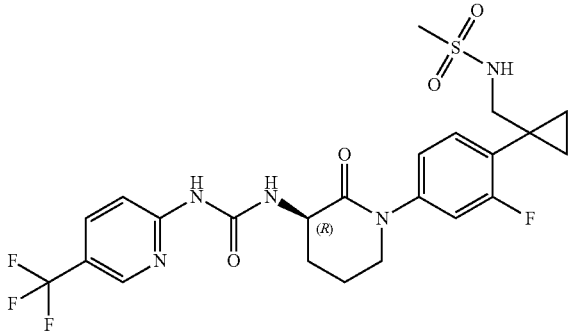<br>(R)-N-((1-(2-fluoro-4-(2-oxo-3-(3-(5-(trifluoromethyl)pyridin-2-yl)ureido)piperidin-1-yl)phenyl)cyclopropyl)methyl)methanesulfonamide | 544.2 | Method F, RT = 1.604 min, 94.5% | ¹H NMR (400 MHz, DMSO-d6): δ 9.80 (s, 1H), 8.55 (s, 1H), 8.15 (d, J = 5.9 Hz, 1H), 8.08-7.99 (m, 1H), 7.69 (d, J = 9.0 Hz, 1H), 7.35 (t, J = 8.4 Hz, 1H), 7.21-7.14 (m, 1H), 7.12-6.99 (m, 2H), 4.460-4.33 (m, 1H), 3.75-3.63 (m, 2H), 3.11 (d, J = 6.4 Hz, 2H), 2.69 (s, 3H), 2.34-2.28 (m, 1H), 2.05-1.90 (m, 2H), 1.86-1.73 (m, 1H), 0.96-0.82 (m, 2H), 0.81-0.66 (m, 2H). |
| 27 | 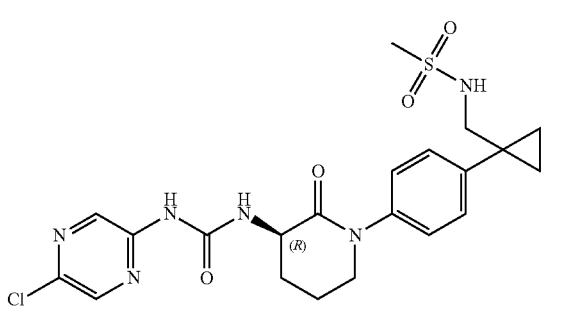<br>(R)-N-((1-(4-(3-(5-chloropyrazin-2-yl)ureido)-2-oxopiperidin-1-yl)phenyl)cyclopropyl)methyl)methanesulfonamide | 493.2 | Method F, RT = 1.306 min, 100% | ¹H NMR (DMSO-d6, 400 MHz): δ 9.74 (s, 1H), 8.86 (s, 1H), 8.37 (s, 1H), 7.46 (d, J = 6.4 Hz, 1H), 7.34 (t, J = 8.3 Hz, 1H), 7.22 (t, J = 8.1 Hz, 2H), 7.05 (t, J = 6.2 Hz, 1H), 4.46-4.29 (m, 1H), 3.73-3.57 (m, 2H), 3.13 (d, J = 6.2 Hz, 2H), 2.72 (s, 3H), 2.35-2.29 (m, 1H), 2.00-1.98 (m, 2H), 1.89-1.73 (m, 1H), 0.96-0.86 (m, 2H), 0.81-0.68 (m, 2H). |
| 28 | 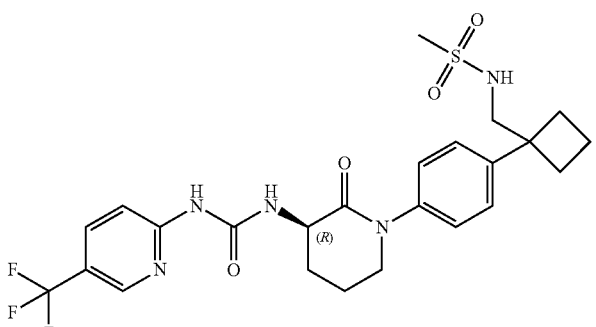<br>(R)-N-((1-(4-(2-oxo-3-(3-(5-(trifluoromethyl)pyridin-2-yl)ureido)piperidin-1-yl)phenyl)cyclobutyl)methyl)methanesulfonamide | 540.2 | Method F, RT = 1.695 min, 99.5% | ¹H NMR (400 MHz, DMSO-d6): δ 9.78 (s, 1H), 8.54 (s, 1H), 8.12 (d, J = 6.6 Hz, 1H), 8.07-8.00 (m, 1H), 7.71 (d, J = 8.8 Hz, 1H), 7.25 (d, J = 8.3 Hz, 2H), 7.16 (d, J = 8.3 Hz, 2H), 6.92 (t, J = 6.6 Hz, 1H), 4.42-4.34 (m, 1H), 3.71-3.63 (m, 2H), 3.13 (d, J = 6.6 Hz, 2H), 2.62 (s, 3H), 2.35-2.15 (m, 5H), 2.04-1.93 (m, 3H), 1.87-1.72 (m, 2H). |

TABLE 1-continued

| Ex | Structure and Name | LCMS (M + H)+ | HPLC Method, RT (min.) & Purity | ¹H NMR |
|---|---|---|---|---|
| 29 | 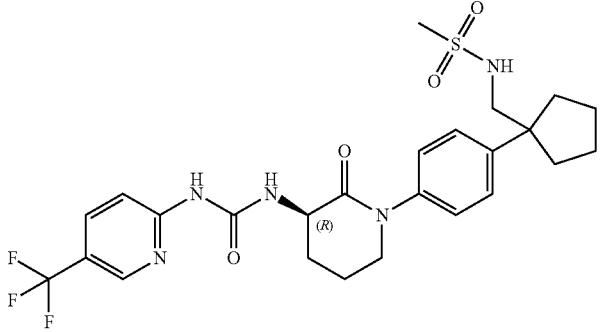<br>(R)-N-((1-(4-(2-oxo-3-(3-(5-(trifluoromethyl)pyridin-2-yl)ureido)piperidin-1-yl)phenyl)cyclopentyl)methyl)methanesulfonamide | 554.3 | Method F, RT = 1.780 min, 99.5% | ¹H NMR (400 MHz, DMSO-d6): δ 9.79 (s, 1H), 8.54 (s, 1H), 8.13 (d, J = 6.4 Hz, 1H), 8.04 (dd, J = 8.9, 2.1 Hz, 1H), 7.71 (d, J = 8.8 Hz, 1H), 7.34 (d, J = 8.6 Hz, 2H), 7.19 (d, J = 8.6 Hz, 2H), 6.68 (t, J = 6.8 Hz, 1H), 4.48-4.31 (m, 1H), 3.75-3.56 (m, 2H), 3.06 (d, J = 6.8 Hz, 2H), 2.58 (s, 3H), 2.36-2.28 (m, 1H), 2.04-1.94 (m, 4H), 1.85-1.62 (m, 5H), 1.64-1.58 (m, 2H). |
| 30 | 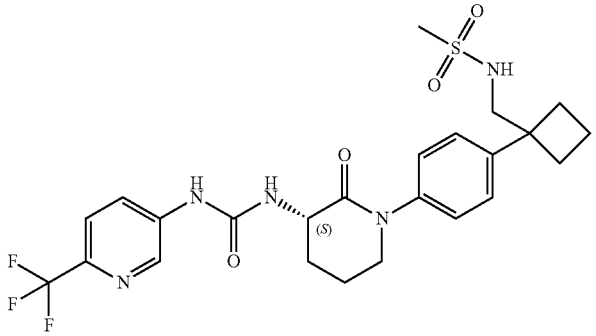<br>(S)-N-((1-(4-(2-oxo-3-(3-(6-(trifluoromethyl)pyridin-3-yl)ureido)piperidin-1-yl)phenyl)cyclobutyl)methyl)methanesulfonamide | 540.2 | Method F, RT = 1.580 min, 100% | ¹H NMR (400 MHz, DMSO-d6): δ 9.62 (s, 1H), 8.69 (d, J = 2.2 Hz, 1H), 8.14 (d, J = 8.6 Hz, 1H), 7.76 (d, J = 8.6 Hz, 1H), 7.24 (d, J = 8.3 Hz, 2H), 7.17 (d, J = 8.3 Hz, 2H), 7.01 (d, J = 6.6 Hz, 1H), 6.97-6.86 (m, 1H), 4.36-4.29 (m, 1H), 3.65 (d, J = 6.8 Hz, 2H), 3.20 (d, J = 6.6 Hz, 2H), 2.61 (s, 3H), 2.32-2.18 (m, 5H), 2.03-1.91 (m, 3H), 1.86-1.69 (m, 2H). |
| 31 | 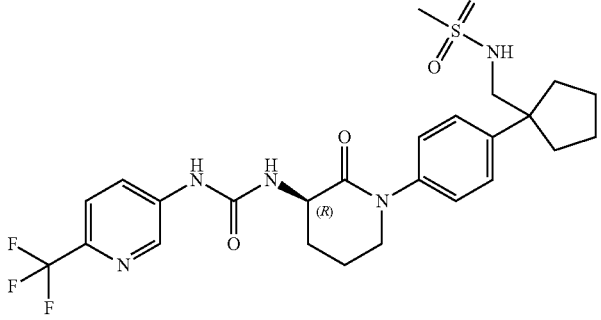<br>(R)-N-((1-(4-(2-oxo-3-(3-(6-(trifluoromethyl)pyridin-3-yl)ureido)piperidin-1-yl)phenyl)cyclopentyl)methyl)methanesulfonamide | 554.2 | Method F, RT = 1.667 min, 100% | ¹H NMR (400 MHz, DMSO-d6): δ 9.44 (s, 1H), 8.68 (d, J = 2.2 Hz, 1H), 8.15 (dd, J = 8.7, 2.3 Hz, 1H), 7.76 (d, J = 8.6 Hz, 1H), 7.32 (d, J = 8.6 Hz, 2H), 7.24 (d, J = 8.3 Hz, 2H), 6.87 (t, J = 6.6 Hz, 1H), 6.73-6.68 (m, 1H), 4.44-4.24 (m, 1H), 3.66 (tq, J = 12.1, 6.1 Hz, 2H), 3.06 (d, J = 6.6 Hz, 2H), 2.57 (s, 3H), 2.06-1.90 (m, 5H), 1.87-1.63 (m, 5H), 1.64-1.58 (m, 2H). |

TABLE 1-continued

| Ex | Structure and Name | LCMS (M + H)+ | HPLC Method, RT (min.) & Purity | ¹H NMR |
|---|---|---|---|---|
| 32 | 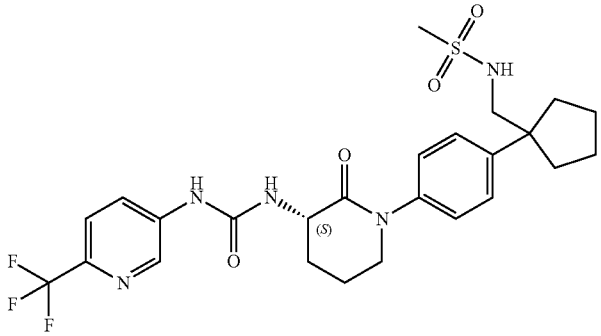<br>(S)-N-((1-(4-(2-oxo-3-(3-(6-(trifluoromethyl)pyridin-3-yl)ureido)piperidin-1-yl)phenyl)cyclopentyl)methyl)methanesulfonamide | 554.2 | Method F, RT = 1.667 min, 100% | ¹H NMR (400 MHz, DMSO-d6): δ 9.44 (s, 1H), 8.68 (d, J = 2.2 Hz, 1H), 8.15 (dd, J = 8.7, 2.3 Hz, 1H), 7.76 (d, J = 8.6 Hz, 1H), 7.32 (d, J = 8.6 Hz, 2H), 7.24 (d, J = 8.3 Hz, 2H), 6.87 (t, J = 6.6 Hz, 1H), 6.74-6.69 (m, 1H), 4.44-4.24 (m, 1H), 3.66 (tq, J = 12.1, 6.1 Hz, 2H), 3.06 (d, J = 6.6 Hz, 2H), 2.57 (s, 3H), 2.06-1.90 (m, 5H), 1.87-1.63 (m, 5H), 1.64-1.59 (m, 2H). |
| 33 | 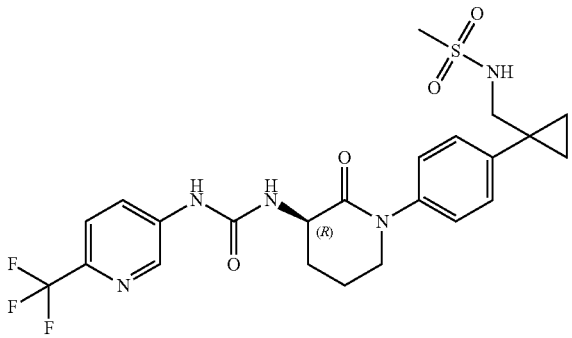<br>(R)-N-((1-(4-(2-oxo-3-(3-(6-(trifluoromethyl)pyridin-3-yl)ureido)piperidin-1-yl)phenyl)cyclopropyl)methyl)methanesulfonamide | 526.2 | Method F, RT = 1.447 min, 98.5% | ¹H NMR (400 MHz, DMSO-d6): δ 9.45 (s, 1H), 8.67 (d, J = 2.4 Hz, 1H), 8.15 (dd, J = 8.6, 2.4 Hz, 1H), 7.76 (d, J = 8.8 Hz, 1H), 7.42-7.29 (m, 2H), 7.20 (d, J = 8.6 Hz, 2H), 7.05 (t, J = 6.1 Hz, 1H), 6.83 (d, J = 6.6 Hz, 1H), 4.41-4.24 (m, 1H), 3.75-3.59 (m, 2H), 3.14 (d, J = 6.6 Hz, 2H), 2.72 (s, 3H), 2.32-2.25 (m, 1H), 2.05-1.90 (m, 2H), 1.87-1.72 (m, 1H), 0.97-0.84 (m, 2H), 0.83-0.69 (m, 2H). |
| 34 | 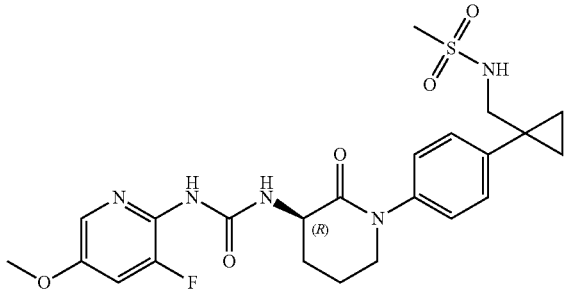<br>(R)-N-((1-(4-(3-(3-fluoro-5-methoxypyridin-2-yl)ureido)-2-oxopiperidin-1-yl)phenyl)cyclopropyl)methyl)methanesulfonamide | 506.2 | Method F, RT = 1.320 min, 100% | ¹H NMR (400 MHz, DMSO-d6): δ 8.85 (s, 1H), 8.58 (br. s., 1H), 7.83 (d, J = 2.2 Hz, 1H), 7.48 (dd, J = 11.7, 2.4 Hz, 1H), 7.33 (d, J = 8.6 Hz, 2H), 7.21 (d, J = 8.3 Hz, 2H), 7.04 (t, J = 6.6 Hz, 1H), 4.44-4.31 (m, 1H), 3.80 (s, 3H), 3.71-3.59 (m, 2H), 3.18 (d, J = 6.6 Hz, 2H), 2.73 (s, 3H), 2.36-2.32 (m, 1H), 2.09-1.91 (m, 2H), 1.87-1.72 (m, 1H), 0.9-0.85 (m, 2H), 0.82-0.74 (m, 2H). |

TABLE 1-continued

| Ex | Structure and Name | LCMS (M + H)+ | HPLC Method, RT (min.) & Purity | ¹H NMR |
|---|---|---|---|---|
| 35 | 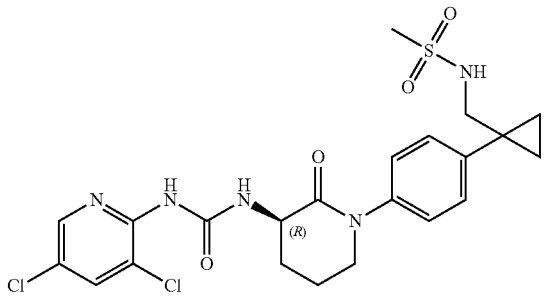(R)-N-((1-(4-(3-(3-(3,5-dichloropyridin-2-yl)ureido)-2-oxopiperidin-1-yl)phenyl)cyclopropyl)methyl)methanesulfonamide | 526.1 | Method F, RT = 1.567 min, 100% | ¹H NMR (400 MHz, DMSO-d6): δ 8.93 (d, J = 5.9 Hz, 1H), 8.51-8.42 (br s, 1H), 8.28 (br. s, 1H), 8.19 (d, J = 2.2 Hz, 1H), 7.33 (d, J = 8.6 Hz, 2H), 7.22 (d, J = 8.3 Hz, 2H), 7.04 (t, J = 6.6 Hz, 1H), 4.51-4.31 (m, 1H), 3.74-3.56 (m, 2H), 3.18 (d, J = 6.6 Hz, 2H), 2.73 (s, 3H), 2.36-2.32 (m, 1H), 2.03-1.91 (m, 2H), 1.88-1.74 (m, 1H), 0.95-0.83 (m, 2H), 0.83-0.68 (m, 2H). |
| 36 | 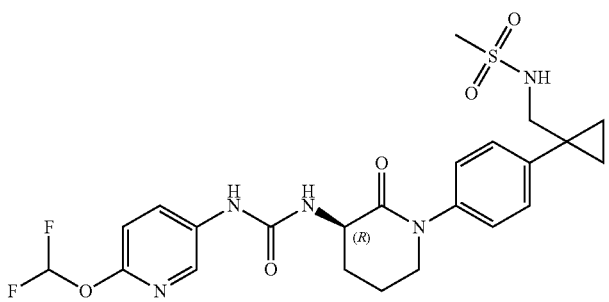(R)-N-((1-(4-(3-(3-(6-(difluoromethoxy)pyridin-3-yl)ureido)-2-oxopiperidin-1-yl)phenyl)cyclopropyl)methyl)methanesulfonamide | 524.2 | Method F, RT = 1.410 min, 100% | ¹H NMR (400 MHz, DMSO-d6): δ 8.98 (s, 1H), 8.26 (d, J = 2.4 Hz, 1H), 7.95 (dd, J = 8.8, 2.2 Hz, 1H), 7.67 (s, 1H), 7.34 (d, J = 8.6 Hz, 2H), 7.22 (d, J = 8.3 Hz, 2H), 7.05 (t, J = 6.1 Hz, 1H), 7.00 (d, J = 9.0 Hz, 1H), 6.63 (d, J = 6.8 Hz, 1H), 4.32-4.29 (m, 1H), 3.71-3.59 (m, 2H), 3.19 (d, J = 6.1 Hz, 2H), 2.72 (s, 3H), 2.29-2.25 (m, 1H), 1.96-1.90 (m, 2H), 1.85-1.69 (m, 1H), 0.94-0.85 (m, 2H), 0.83-0.68 (m, 2H). |
| 37 | 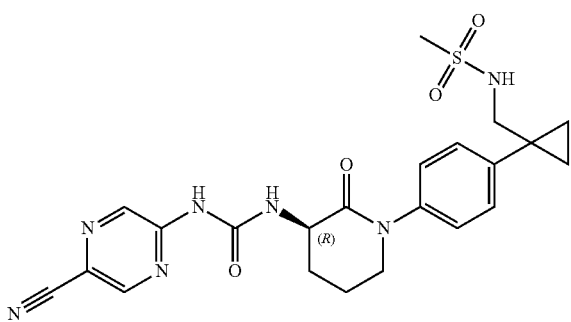(R)-N-((1-(4-(3-(3-(5-cyanopyrazin-2-yl)ureido)-2-oxopiperidin-1-yl)phenyl)cyclopropyl)methyl)methanesulfonamide | 484.2 | Method F, RT = 1.231 min, 100% | ¹H NMR (400 MHz, DMSO-d6): δ 10.27 (s, 1H), 9.06 (s, 1H), 8.79 (s, 1H), 7.82 (d, J = 6.6 Hz, 1H), 7.34 (d, J = 8.3 Hz, 2H), 7.24 (d, J = 8.3 Hz, 2H), 7.05 (t, J = 6.6 Hz, 1H), 4.42-4.37 (m, 1H), 3.77-3.56 (m, 2H), 3.16 (d, J = 6.6 Hz, 2H), 2.72 (s, 3H), 2.40-2.32 (m, 1H), 2.08-1.91 (m, 2H), 1.87-1.71 (m, 1H), 0.98-0.85 (m, 2H), 0.85-0.69 (m, 2H). |

TABLE 1-continued

| Ex | Structure and Name | LCMS (M + H)+ | HPLC Method, RT (min.) & Purity | ¹H NMR |
|---|---|---|---|---|
| 38 | 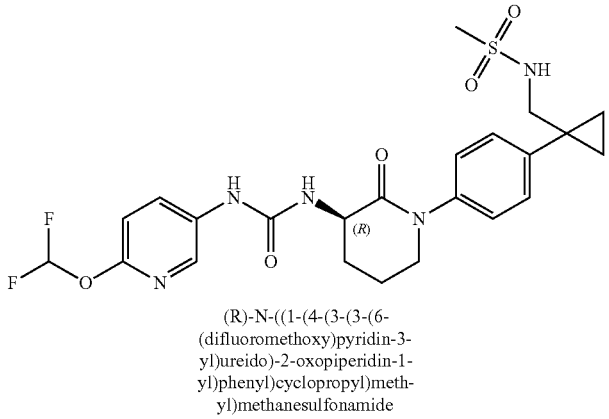<br>(R)-N-((1-(4-(3-(3-(6-(difluoromethoxy)pyridin-3-yl)ureido)-2-oxopiperidin-1-yl)phenyl)cyclopropyl)methyl)methanesulfonamide | 524.2 | Method F, RT = 1.409 min, 100% | ¹H NMR (400 MHz, DMSO-d6): δ 8.98 (s, 1H), 8.26 (d, J = 2.4 Hz, 1H), 7.95 (dd, J = 8.8, 2.2 Hz, 1H), 7.67 (s, 1H), 7.34 (d, J = 8.6 Hz, 2H), 7.22 (d, J = 8.3 Hz, 2H), 7.05 (t, J = 6.1 Hz, 1H), 7.00 (d, J = 9.0 Hz, 1H), 6.63 (d, J = 6.8 Hz, 1H), 4.32-4.29 (m, 1H), 3.71-3.59 (m, 2H), 3.19 (d, J = 6.1 Hz, 2H), 2.72 (s, 3H), 2.29-2.25 (m, 1H), 1.96-1.90 (m, 2H), 1.85-1.69 (m, 1H), 0.94-0.85 (m, 2H), 0.83-0.68 (m, 2H). |
| 39 | 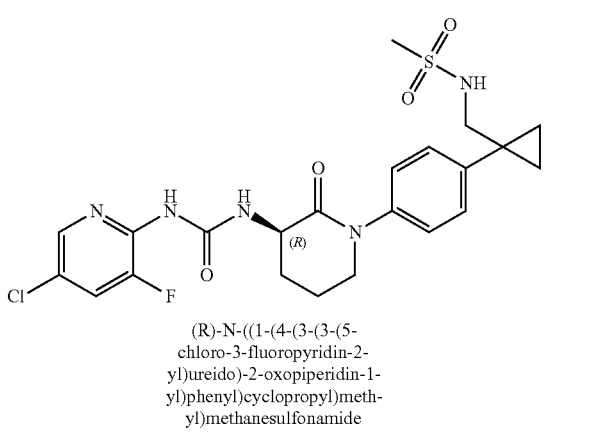<br>(R)-N-((1-(4-(3-(3-(5-chloro-3-fluoropyridin-2-yl)ureido)-2-oxopiperidin-1-yl)phenyl)cyclopropyl)methyl)methanesulfonamide | 510.1 | Method F, RT = 1.446 min, 98.9% | ¹H NMR (400 MHz, DMSO-d6): δ 9.36 (s, 1H), 8.82 (d, J = 5.4 Hz, 1H), 8.14 (d, J = 2.0 Hz, 1H), 8.00 (dd, J = 10.0, 2.0 Hz, 1H), 7.38 (d, J = 8.3 Hz, 2H), 7.22 (d, J = 8.3 Hz, 2H), 7.05 (t, J = 6.4 Hz, 1H), 4.43-4.38 (m, 1H), 3.75-3.57 (m, 2H), 3.16 (d, J = 6.4 Hz, 2H), 2.73 (s, 3H), 2.36-2.32 (m, 1H), 2.09-1.91 (m, 2H), 1.87-1.72 (m, 1H), 0.97-0.85 (m, 2H), 0.83-0.69 (m, 2H). |
| 40 | 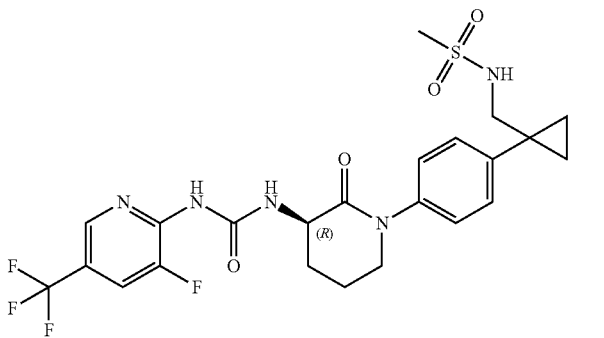<br>(R)-N-((1-(4-(3-(3-(3-fluoro-5-(trifluoromethyl)pyridin-2-yl)ureido)-2-oxopiperidin-1-yl)phenyl)cyclopropyl)methyl)methanesulfonamide | 544.2 | Method F, RT = 1.571 min, 100% | ¹H NMR (400 MHz, DMSO-d6): δ 9.75 (s, 1H), 9.26 (d, J = 5.6 Hz, 1H), 8.44 (s, 1H), 8.18 (d, J = 11.2 Hz, 1H), 7.35 (d, J = 8.3 Hz, 2H), 7.20 (d, J = 8.3 Hz, 2H), 7.04 (t, J = 6.6 Hz, 1H), 4.51-4.36 (m, 1H), 3.74-3.61 (m, 2H), 3.19 (d, J = 6.6 Hz, 2H), 2.73 (s, 3H), 2.39-2.32 (m, 1H), 2.04-1.92 (m, 2H), 1.89-1.77 (m, 1H), 0.98-0.86 (m, 2H), 0.84-0.69 (m, 2H). |

TABLE 1-continued

| Ex | Structure and Name | LCMS (M + H)+ | HPLC Method, RT (min.) & Purity | ¹H NMR |
|---|---|---|---|---|
| 41 | 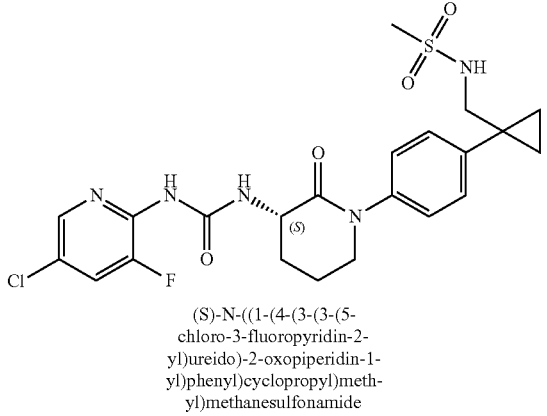<br>(S)-N-((1-(4-(3-(3-(5-chloro-3-fluoropyridin-2-yl)ureido)-2-oxopiperidin-1-yl)phenyl)cyclopropyl)methyl)methanesulfonamide | 510.1 | Method F, RT = 1.446 min, 100% | ¹H NMR (400 MHz, DMSO-d6): δ 9.36 (s, 1H), 8.82 (d, J = 5.4 Hz, 1H), 8.14 (d, J = 2.0 Hz, 1H), 8.00 (dd, J = 10.0, 2.0 Hz, 1H), 7.38 (d, J = 8.3 Hz, 2H), 7.22 (d, J = 8.3 Hz, 2H), 7.05 (t, J = 6.4 Hz, 1H), 4.43-4.38 (m, 1H), 3.75-3.57 (m, 2H), 3.19 (d, J = 6.4 Hz, 2H), 2.73 (s, 3H), 2.36-2.32 (m, 1H), 2.09-1.91 (m, 2H), 1.87-1.72 (m, 1H), 0.97-0.85 (m, 2H), 0.83-0.69 (m, 2H). |
| 42 | 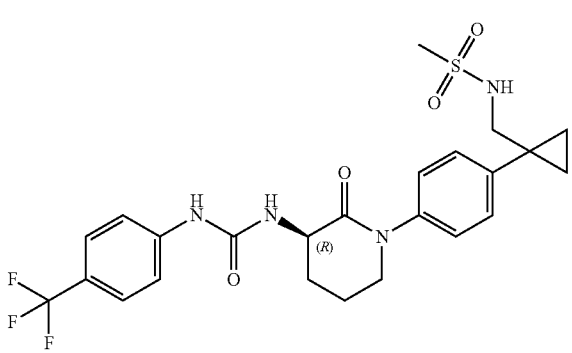<br>(R)-N-((1-(4-(2-oxo-3-(3-(4-(trifluoromethyl)phenyl)ureido)piperidin-1-yl)phenyl)cyclopropyl)methyl)methanesulfonamide | 525.2 | Method F, RT = 1.662 min, 94.6% | ¹H NMR (400 MHz, DMSO-d6): δ 9.21 (s, 1H), 7.68-7.48 (m, 4H), 7.42-7.29 (m, J = 8.6 Hz, 2H), 7.28-7.15 (m, J = 8.6 Hz, 2H), 7.07-7.03 (m, 1H), 6.67 (d, J = 6.6 Hz, 1H), 4.40-4.24 (m, 1H), 3.74-3.55 (m, 2H), 3.19 (d, J = 4.2 Hz, 2H), 2.73 (s, 3H), 2.33-2.24 (m, 1H), 2.05-1.88 (m, 2H), 1.84-1.70 (m, 1H), 0.94-0.83 (m, 2H), 0.82-0.71 (m, 2H). |
| 43 | 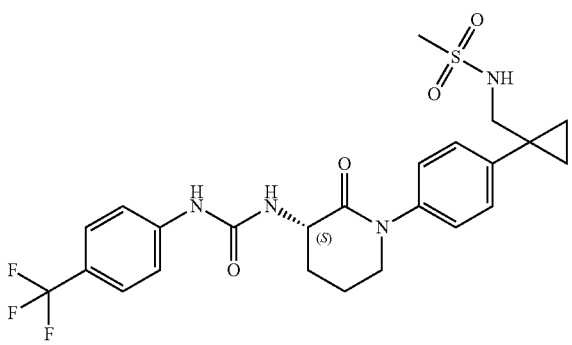<br>(S)-N-((1-(4-(2-oxo-3-(3-(4-(trifluoromethyl)phenyl)ureido)piperidin-1-yl)phenyl)cyclopropyl)methyl)methanesulfonamide | 525.2 | Method F, RT = 1.666 min, 100% | ¹H NMR (400 MHz, DMSO-d6): δ 9.21 (s, 1H), 7.68-7.48 (m, 4H), 7.42-7.29 (m, J = 8.6 Hz, 2H), 7.28-7.15 (m, J = 8.6 Hz, 2H), 7.07-7.03 (m, 1H), 6.67 (d, J = 6.6 Hz, 1H), 4.40-4.24 (m, 1H), 3.74-3.55 (m, 2H), 3.19 (d, J = 4.2 Hz, 2H), 2.73 (s, 3H), 2.33-2.24 (m, 1H), 2.05-1.88 (m, 2H), 1.84-1.70 (m, 1H), 0.94-0.83 (m, 2H), 0.82-0.71 (m, 2H). |

TABLE 1-continued

| Ex | Structure and Name | LCMS (M + H)+ | HPLC Method, RT (min.) & Purity | ¹H NMR |
|---|---|---|---|---|
| 45 | 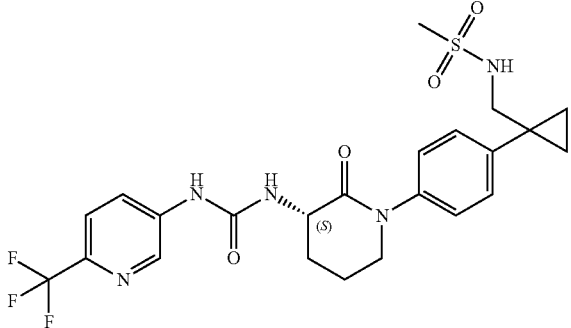<br>(S)-N-((1-(4-(2-oxo-3-(3-(6-(trifluoromethyl)pyridin-3-yl)ureido)piperidin-1-yl)phenyl)cyclopropyl)methyl)methanesulfonamide | 526.2 | Method F, RT = 1.418 min, 100% | ¹H NMR (400 MHz, DMSO-d6): δ 9.45 (s, 1H), 8.67 (d, J = 2.4 Hz, 1H), 8.15 (dd, J = 8.6, 2.4 Hz, 1H), 7.76 (d, J = 8.8 Hz, 1H), 7.42-7.29 (m, 2H), 7.20 (d, J = 8.6 Hz, 2H), 7.05 (t, J = 6.1 Hz, 1H), 6.83 (d, J = 6.6 Hz, 1H), 4.41-4.24 (m, 1H), 3.75-3.59 (m, 2H), 3.19 (d, J = 6.1 Hz, 2H), 2.72 (s, 3H), 2.32-2.25 (m, 1H), 2.05-1.90 (m, 2H), 1.87-1.72 (m, 1H), 0.97-0.84 (m, 2H), 0.83-0.69 (m, 2H). |
| 46 | 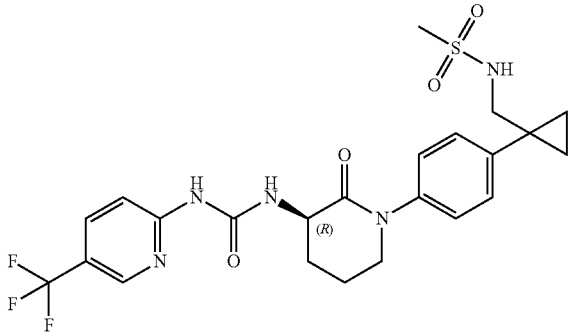<br>(R)-N-((1-(4-(2-oxo-3-(5-(trifluoromethyl)pyridin-2-yl)ureido)piperidin-1-yl)phenyl)cyclopropyl)methyl)methanesulfonamide | 526.2 | Method F, RT = 1.549 min, 98.5% | ¹H NMR (400 MHz, DMSO-d6): δ 9.81 (s, 1H), 8.55 (s, 1H), 8.11 (br. s., 1H), 8.05 (dd, J = 8.9, 2.3 Hz, 1H), 7.71 (d, J = 8.8 Hz, 1H), 7.33 (d, J = 8.3 Hz, 2H), 7.22 (d, J = 8.3 Hz, 2H), 7.07 (t, J = 6.2 Hz, 1H), 4.45-4.31 (m, 1H), 3.74-3.59 (m, 2H), 3.16 (d, J = 6.2 Hz, 2H), 2.72 (s, 3H), 2.38-2.29 (m, 1H), 2.03-1.94 (m, 2H), 1.87-1.69 (m, 1H), 0.96-0.85 (m, 2H), 0.83-0.69 (m, 2H). |
| 47 | 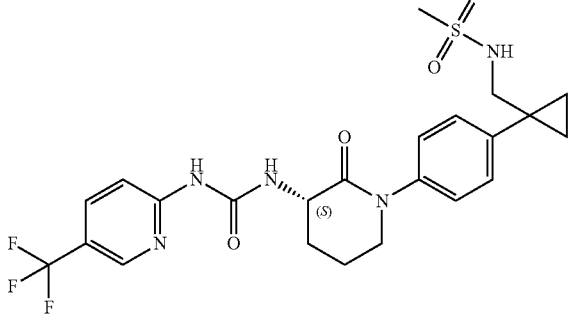<br>(S)-N-((1-(4-(2-oxo-3-(3-(5-(trifluoromethyl)pyridin-2-yl)ureido)piperidin-1-yl)phenyl)cyclopropyl)methyl)methanesulfonamide | 526.2 | Method F, RT = 1.538 min, 100% | ¹H NMR (400 MHz, DMSO-d6): δ 9.81 (s, 1H), 8.55 (s, 1H), 8.13-8.09 (m, 1H), 8.05 (dd, J = 8.9, 2.3 Hz, 1H), 7.71 (d, J = 8.8 Hz, 1H), 7.33 (d, J = 8.3 Hz, 2H), 7.22 (d, J = 8.3 Hz, 2H), 7.07 (t, J = 6.2 Hz, 1H), 4.45-4.31 (m, 1H), 3.74-3.59 (m, 2H), 3.19 (d, J = 6.2 Hz, 2H), 2.72 (s, 3H), 2.38-2.29 (m, 1H), 2.03-1.94 (m, 2H), 1.87-1.69 (m, 1H), 0.96-0.85 (m, 2H), 0.83-0.69 (m, 2H). |

TABLE 1-continued

| Ex | Structure and Name | LCMS (M + H)+ | HPLC Method, RT (min.) & Purity | ¹H NMR |
|---|---|---|---|---|
| 48 | 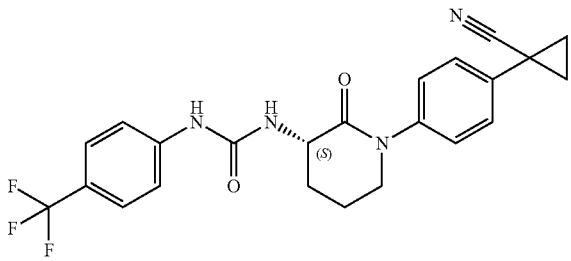<br>(S)-1-(1-(4-(1-cyanocyclopropyl)phenyl)-2-oxopiperidin-3-yl)-3-(4-(trifluoromethyl)phenyl)urea | 443 | Method F, RT = 2.02 min, 99.6% | ¹H NMR (400 MHz, DMSO-d6): δ 9.20 (s, 1H), 7.63-7.54 (m, 4H), 7.38-7.30 (m, 4H), 6.67 (d, J = 6.8 Hz, 1H), 4.37-4.29 (m, 1H), 3.74-3.59 (m, 2H), 2.34-2.25 (m, 1H), 2.03-1.94 (m, 2H), 1.85-1.79 (m, 1H), 1.77-1.72 (m, 2H), 1.53-1.48 (m, 2H). |
| 49 | 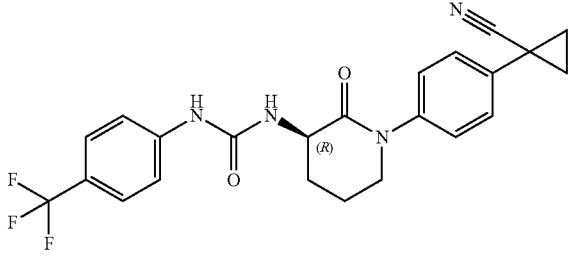<br>(S)-1-(1-(4-(1-cyanocyclopropyl)phenyl)-2-oxopiperidin-3-yl)-3-(4-(trifluoromethyl)phenyl)urea | 443 | Method F, RT = 2.019 min, 100% | ¹H NMR (400 MHz, DMSO-d6): δ 9.20 (s, 1H), 7.63-7.54 (m, 4H), 7.38-7.30 (m, 4H), 6.67 (d, J = 6.8 Hz, 1H), 4.37-4.29 (m, 1H), 3.74-3.59 (m, 2H), 2.34-2.25 (m, 1H), 2.03-1.94 (m, 2H), 1.85-1.79 (m, 1H), 1.77-1.72 (m, 2H), 1.53-1.48 (m, 2H). |
| 50 | 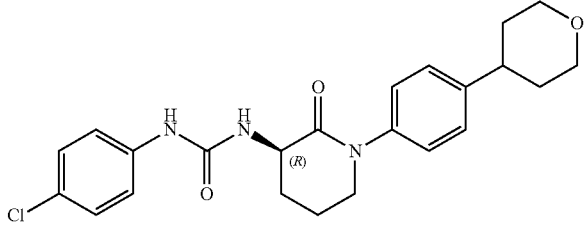<br>(R)-1-(4-chlorophenyl)-3-(2-oxo-1-(4-(tetrahydro-2H-pyran-4-yl)phenyl)piperidin-3-yl)urea | 428.1 | Method F, RT = 1.89 min, 100% | ¹H NMR (400 MHz, DMSO-d6): δ 8.91 (s, 1H), 7.42 (d, J = 9.20 Hz, 2H), 7.25-7.28 (m, 4H), 7.20-7.23 (m, 2H), 6.54 (d, J = 6.40 Hz, 1H), 4.27-4.30 (m, 1H), 3.93-3.96 (m, 2H), 3.62-3.67 (m, 2H), 3.42-3.46 (m, 2H), 2.77-2.81 (m, 1H), 2.28-2.29 (m, 1H), 1.95-1.98 (m, 2H), 1.64-1.70 (m, 5H). |
| 51 | 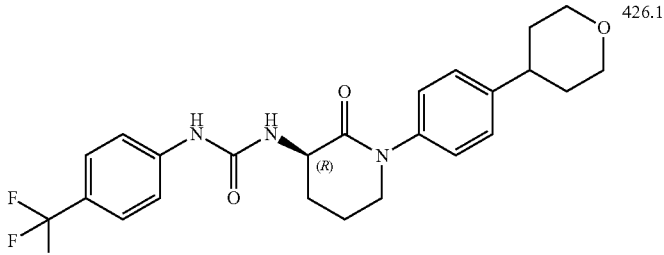<br>(R)-1-(2-oxo-1-(4-(tetrahydro-2H-pyran-4-yl)phenyl)piperidin-3-yl)-3-(4-(trifluoromethyl)phenyl)urea | 426.1 | Method F, RT = 2.06 min, 96% | ¹H NMR (400 MHz, DMSO-d6): δ 9.21 (s, 1H), 7.57 (dd, J = 9.60 Hz, 3.2Hz, 4H), 7.26-7.22 (m, 4H), 6.66 (d, J = 6.80 Hz, 1H), 4.30-4.33 (m, 1H), 3.93-3.97 (m, 2H), 3.64-3.68 (m, 2H), 3.40-3.46 (m, 2H), 2.73-2.78 (m, 1H), 2.27-2.24 (m, 1H), 1.96-1.99 (m, 2H), 1.64-1.71 (m, 5H). |

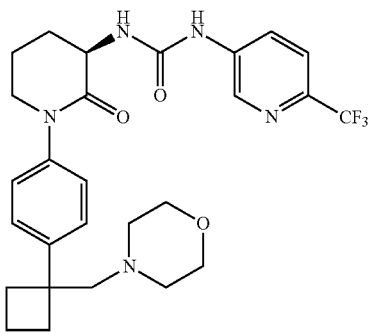 [SMILES: O=C(Nc1ccc(C(F)(F)F)nc1)N[C@@H]1CCCN(c2ccc(C3(CN4CCOCC4)CCC3)cc2)C1=O]

Example 52A:
1-(4-Bromophenyl)cyclobutane-1-carbaldehyde

To a solution of 1-(4-bromophenyl)cyclobutane-1-carbonitrile (500 mg, 2.1 mmol) in diethyl ether (10 mL) at −10° C., was added diisobutylaluminum hydride (1.9 mL, 2.3 mmol), and the mixture was stirred at −10° C. for two hours. The reaction mixture was quenched with 1 N HCl (20 mL) and extracted with DCM (3×20 mL). The combined organic layers were washed with brine (2×20 mL), dried over $Na_2SO_4$, concentrated under reduced pressure and purified by column chromatography (12% EtOAc-Pet ether) to afford Example 52A (400 mg, 1.7 mmol, 79% yield) as a light yellow liquid. $^1$H NMR (400 MHz, $CDCl_3$): (δ 9.52 (s, 1H), 7.55-7.23 (m, 2H), 7.05-7.00 (m, 2H), 2.75-2.68 (m, 2H), 2.44-2.39 (m, 2H), 2.06-1.88 (m, 2H).

Example 52B: tert-Butyl (1-(4-(1-formylcyclobutyl)phenyl)-2-oxopiperidin-3-yl)carbamate Example 52A (450 mg, 1.9 mmol), and $Cs_2CO_3$ (910 mg, 2.8 mmol) were added to a stirred solution of tert-butyl (2-oxopiperidin-3-yl)carbamate (400 mg, 1.9 mmol) in 1,4-dioxane (4 mL). The reaction mixture was purged with nitrogen for 5 min and charged with Xantphos (110 mg, 0.19 mmol) and $Pd_2(dba)_3$ (85 mg, 0.093 mmol). The reaction mixture was again purged with nitrogen for 3 min and heated at 110° C. for 16 h. The reaction mixture was cooled, filtered through a Celite pad and the filtrate was concentrated under reduced pressure. The crude compound was purified using column chromatography (EtOAc-Pet ether) to afford Example 52B (240 mg, 0.63 mmol, 34% yield) as a brown solid. $^1$H NMR (400 MHz, $CDCl_3$): δ 9.55 (s, 1H), 7.27-7.20 (m, 2H), 7.18-7.13 (m, 2H), 5.52 (br. s., 1H), 4.28-4.18 (m, 1H), 3.73-3.62 (m, 2H), 2.77-2.69 (m, 2H), 2.63-2.58 (m, 1H), 2.44-2.32 (m, 2H), 2.08-1.85 (m, 4H), 1.73-1.67 (m, 1H), 1.45 (s, 9H).

Example 52C: tert-Butyl (1-(4-(1-(morpholinomethyl)cyclobutyl)phenyl)-2-oxopiperidin-3-yl)carbamate Morpholine (0.058 mL, 0.67 mmol) and sodium triacetoxyborohydride (210 mg, 1.0 mmol) were added to a stirred solution of Example 52B (250 mg, 0.67 mmol) in 1,2-dichloroethane (2 mL) under argon atmosphere. The resulting reaction mixture was stirred for 48 h at rt. The reaction mixture was quenched with an aqueous saturated $NaHCO_3$ (20 mL) solution and extracted with DCM (2×30 mL). The combined organic layers were washed with brine (20 mL), dried over $Na_2SO_4$ and concentrated under reduced pressure to afford crude Example 52C (260 mg, 0.59 mmol, 87% yield) as a brown solid. The crude residue was carried forward to the next step without further purification. MS(ESI) m/z: 444.6 $(M+H)^+$.

Example 52D: 3-Amino-1-(4-(1-(morpholinomethyl)cyclobutyl)phenyl)piperidin-2-one hydrochloride To an ice cooled solution of Example 52C (260 mg, 0.586 mmol) in 1,4-dioxane (2 mL), was added 4 N HCl in 1,4-dioxane (2.2 mL, 8.9 mmol), and the reaction mixture was stirred at rt for two hours. The solvent was evaporated and dried under reduced pressure to obtain a gummy solid. The solid was triturated with diethyl ether (2×20 mL) and dried to afford Example 52D (200 mg, 0.53 mmol, 90% yield) as a brown solid. MS(ESI) m/z: 344.6 $(M+H)^+$.

Example 52: (R)-1-(1-(4-(1-(Morpholinomethyl)cyclobutyl)phenyl)-2-oxopiperidin-3-yl)-3-(6-(trifluoromethyl)pyridin-3-yl)urea DIPEA (0.11 mL, 0.63 mmol) and phenyl (6-(trifluoromethyl)pyridin-3-yl)carbamate (120 mg, 0.42 mmol) were added to an ice cooled suspension of 3-amino-1-(4-(1-(morpholinomethyl)cyclobutyl)phenyl)piperidin-2-one hydrochloride (80 mg, 0.21 mmol) in 1,2-dichloroethane (2 mL). The resulting solution was heated at 50° C. for 15 hours. The reaction mixture was concentrated under reduced pressure to yield the crude compound, which was purified by reverse phase chromatography followed by chiral HPLC to afford Example 52 (21 mg, 0.038 mmol, 18% yield). RT=1.80 min, 99% (Method F); MS(ESI) m/z: 532.3 $(M+H)^+$; $^1$H NMR (400 MHz, DMSO-d6): δ 9.42 (s, 1H), 8.66 (s, 1H), 8.13 (d, J=6.4 Hz, 1H), 7.76 (d, J=8.6 Hz, 1H), 7.25-7.10 (m, 4H), 6.81 (d, J=6.8 Hz, 1H), 4.38-4.25 (m, 1H), 3.41-3.33 (m, 6H), 2.59 (s, 2H), 2.21-2.07 (m, 9H), 1.98 (d, J=6.4 Hz, 3H), 1.86-1.64 (m, 2H).

Additional examples of compounds of this invention shown in Table 2 below were prepared using combinations of the procedures described in Example 52 or modifications thereof known to one skilled in the art of organic synthesis.

| Ex | Structure | Name | LCMS (M + H)+ | HPLC Method, RT (min.) & Purity | ¹H NMR |
|---|---|---|---|---|---|
| 53 | 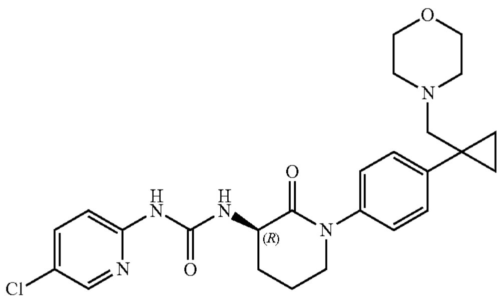 | (R)-1-(5-chloropyridin-2-yl)-3-(1-(4-(1-(morpholinomethyl)cyclopropyl)phenyl)-2-oxopiperidin-3-yl)urea | 484.2 | Method F, RT = 1.698 min, 99.7% | ¹H NMR (400 MHz, DMSO-d6): δ 9.48 (s, 1H), 8.07 (d, J = 2.8 Hz, 1H), 7.97 (d, J = 7.8 Hz, 1H), 7.80 (dd, J = 9.0, 2.7 Hz, 1H), 7.58 (d, J = 8.8 Hz, 1H), 7.35 (d, J = 8.6 Hz, 2H), 7.18 (d, J = 8.6 Hz, 2H), 4.45-4.29 (m, 1H), 3.75-3.59 (m, 2H), 3.46-3.41 (m, 4H), 2.51 (s, 2H), 2.43-2.39 (m, 4H), 2.34-2.25 (m, 1H), 2.05-1.90 (m, 2H), 1.85-1.72 (m, 1H), 0.89-0.67 (m, 4H). |
| 54 | 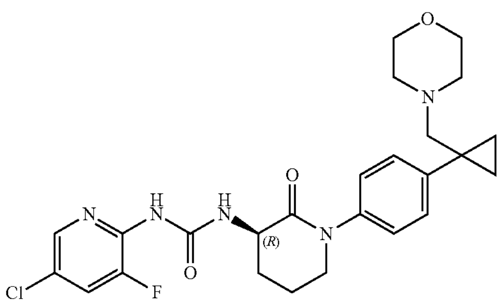 | (R)-1-(5-chloro-3-fluoropyridin-2-yl)-3-(1-(4-(1-(morpholinomethyl)cyclopropyl)phenyl)-2-oxopiperidin-3-yl)urea | 502.2 | Method F, RT = 1.710 min, 100% | ¹H NMR (400 MHz, DMSO-d6): δ 9.37 (s, 1H), 8.87 (d, J = 5.6 Hz, 1H), 8.14 (d, J = 2.2 Hz, 1H), 8.01 (dd, J = 10.1, 2.1 Hz, 1H), 7.35 (d, J = 8.3 Hz, 2H), 7.20 (d, J = 8.3 Hz, 2H), 4.45-4.29 (m, 1H), 3.74-3.60 (m, 2H), 3.52-3.47 (m, 4H), 2.51 (s, 2H), 2.43-2.33 (m, 5H), 2.04-1.92 (m, 2H), 1.86-1.75 (m, 1H), 0.86-0.80 (m, 2H), 0.78-0.72 (m, 2H). |
| 55 | 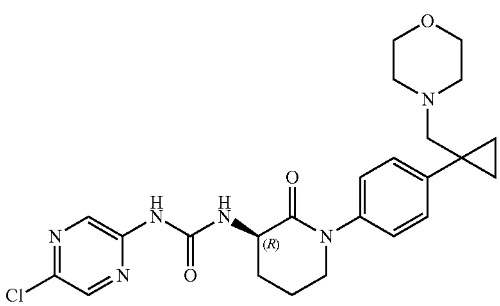 | (R)-1-(5-chloropyrazin-2-yl)-3-(1-(4-(1-(morpholinomethyl)cyclopropyl)phenyl)-2-oxopiperidin-3-yl)urea | 585.3 | Method F, RT = 1.560 min, 99.5% | ¹H NMR (400 MHz, DMSO-d6): δ 9.76 (s, 1H), 8.85 (d, J = 1.5 Hz, 1H), 8.38 (d, J = 1.5 Hz, 1H), 7.48 (d, J = 6.6 Hz, 1H), 7.33 (d, J = 8.6 Hz, 2H), 7.18 (d, J = 8.6 Hz, 2H), 4.45-4.28 (m, 1H), 3.74-3.60 (m, 2H), 3.55-3.47 (m, 4H), 2.51 (s, 2H), 2.43-2.37 m, 4H), 2.38-2.28 (m, 1H), 2.03-1.91 (m, 2H), 1.85-1.72 (m, 1H), 0.84-0.78 (m, 2H), 0.77 0.73 (m, 2H). |
| 56 | 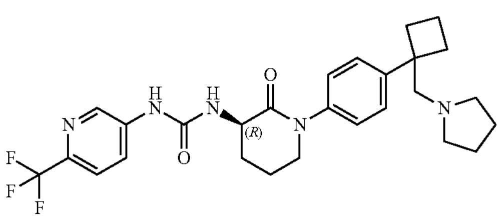 | (R)-1-(2-oxo-1-(4-(1-(pyrrolidin-1-ylmethyl)cyclobutyl)phenyl)piperidin-3-yl)-3-(6-(trifluoromethyl)pyridin-3-yl)urea | 516.3 | Method F, RT = 1.333 min, 100% | ¹H NMR (400 MHz, DMSO-d6): δ 9.44 (br. s., 1H), 8.68 (s, 1H), 8.14 (d, J = 8.6 Hz, 1H), 7.76 (d, J = 9.0 Hz, 1H), 7.26-7.20 (m, 4H), 6.82 (d, J = 6.1 Hz, 1H), 4.39-4.24 (m, 1H), 3.74-3.60 (m, 2H), 2.31-2.08 (m, 9H), 2.05-1.95 (m, 4H), 1.88-1.71 (m, 2H), 1.59-1.53 (m, 5H). |
| 57 | 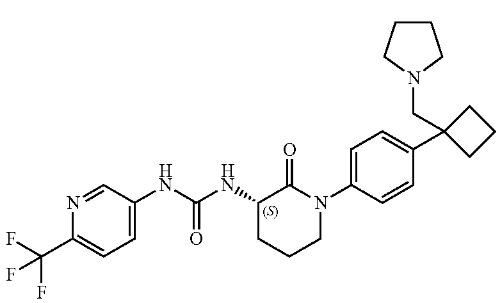 | (S)-1-(2-oxo-1-(4-(1-(pyrrolidin-1-ylmethyl)cyclobutyl)phenyl)piperidin-3-yl)-3-(6-(trifluoromethyl)pyridin-3-yl)urea | 516.3 | Method F, RT = 1.346 min, 100% | ¹H NMR (400 MHz, DMSO-d6): δ 9.44 (br. s., 1H), 8.68 (s, 1H), 8.14 (d, J = 8.6 Hz, 1H), 7.76 (d, J = 9.0 Hz, 1H), 7.26-7.20 (m, 4H), 6.82 (d, J = 6.1 Hz, 1H), 4.39-4.24 (m, 1H), 3.74-3.60 (m, 2H), 2.31-2.08 (m, 9H), 2.05-1.95 (m, 4H), 1.88-1.71 (m, 2H), 1.59-1.53 (m, 5H). |

-continued

| Ex | Structure | Name | LCMS (M + H)+ | HPLC Method, RT (min.) & Purity | ¹H NMR |
|---|---|---|---|---|---|
| 58 | 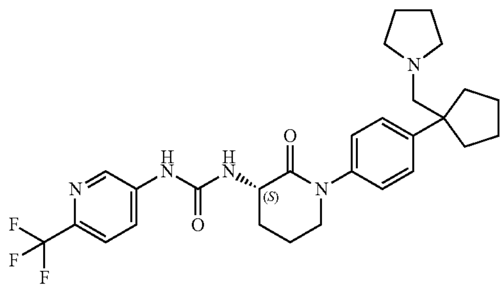 | (S)-1-(2-oxo-1-(4-(1-(pyrrolidin-1-ylmethyl)cyclopentyl)phenyl)piperidin-3-yl)-3-(6-(trifluoromethyl)pyridin-3-yl)urea | 530.3 | Method F, RT = 1.408 min, 100% | ¹H NMR (400 MHz, DMSO-d6): δ 9.59 (s, 1H), 8.68 (d, J = 2.2 Hz, 1H), 8.13 (d, J = 8.6 Hz, 1H), 7.75 (d, J = 8.6 Hz, 1H), 7.30 (d, J = 8.8 Hz, 2H), 7.19 (d, J = 8.6 Hz, 2H), 6.96 (d, J = 7.1 Hz, 1H), 4.37-4.26 (m, 1H), 3.72-3.58 (m, 2H), 2.60 (s, 2H), 2.31-2.22 (m, 1H), 2.21-2.15 (m, 4H), 2.10-2.04 (m, 1H), 2.03-1.87 (m, 3H), 1.85-1.73 (m, 3H), 1.69-1.63 (m, 2H), 1.59-1.55 (m, 2H)., 1.52-1.47 (m, 4H). |
| 59 | 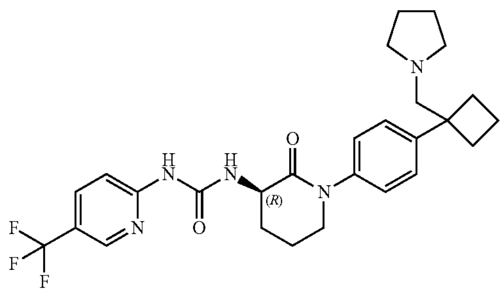 | (R)-1-(2-oxo-1-(4-(1-(pyrrolidin-1-ylmethyl)cyclobutyl)phenyl)piperidin-3-yl)-3-(5-(trifluoromethyl)pyridin-2-yl)urea | 516.3 | Method F, RT = 1.473 min, 100% | ¹H NMR (400 MHz, DMSO-d6): δ 9.78 (s, 1H), 8.54 (s, 1H), 8.17 (br. s., 1H), 8.08-7.98 (m, 1H), 7.68 (d, J = 8.8 Hz, 1H), 7.23-7.16 (m, 4H), 4.44-4.33 (m, 1H), 3.74-3.60 (m, 2H), 2.38-2.30 (m, 4H), 2.28-2.15 (m, 5H), 2.03-1.90 (m, 4H), 1.86-1.68 (m, 2H), 1.55-1.51 (m, 5H). |
| 60 | 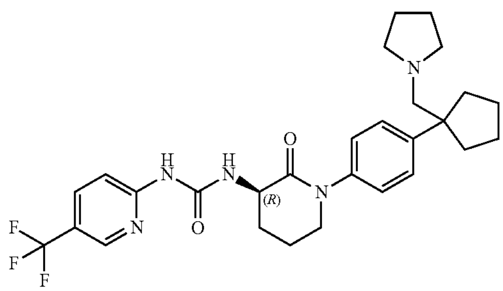 | (R)-1-(2-oxo-1-(4-(1-(pyrrolidin-1-ylmethyl)cyclopentyl)phenyl)piperidin-3-yl)-3-(5-(trifluoromethyl)pyridin-2-yl)urea | 530.3 | Method F, RT = 1.527 min, 100% | ¹H NMR (400 MHz, DMSO-d6): δ 9.78 (s, 1H), 8.54 (s, 1H), 8.18 (br. s., 1H), 8.04 (d, J = 9.0 Hz, 1H), 7.68 (d, J = 8.3 Hz, 1H), 7.31 (d, J = 8.6 Hz, 2H), 7.20 (d, J = 8.6 Hz, 2H), 4.47-4.30 (m, 1H), 3.73-3.66 (m, 2H), 2.65 (m, 2H), 2.35-2.26 (m, 2H), 2.26-2.20 (m, 3H), 2.03-1.86 (m, 4H), 1.85-1.79 (m, 2H), 1.69-1.63 (m, 2H), 1.61-1.36 (m, 7H). |
| 61 | 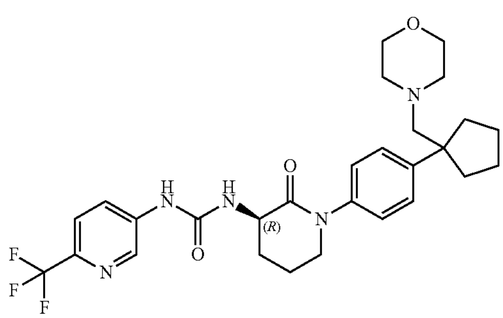 | (R)-1-(1-(4-(1-(morpholinomethyl)cyclopentyl)phenyl)-2-oxopiperidin-3-yl)-3-(6-(trifluoromethyl)pyridin-3-yl)urea | 546.3 | Method F, RT = 1.980 min, 98.9% | ¹H NMR (400 MHz, DMSO-d6): δ 9.40 (s, 1H), 8.66 (d, J = 2.4 Hz, 1H), 8.16-8.06 (m, 1H), 7.75 (d, J = 8.3 Hz, 1H), 7.29 (d, J = 8.6 Hz, 2H), 7.17 (d, J = 8.6 Hz, 2H), 6.79 (d, J = 7.1 Hz, 1H), 4.38-4.23 (m, 1H), 3.73-3.66 (m, 2H), 3.41-3.31 (m, 4H), 2.41 (s, 2H), 2.29-2.21 (m, 1H), 2.14-2.03 (m, 4H), 2.01-1.90 (m, 4H), 1.85-1.50 (m, 7H) |
| 62 | 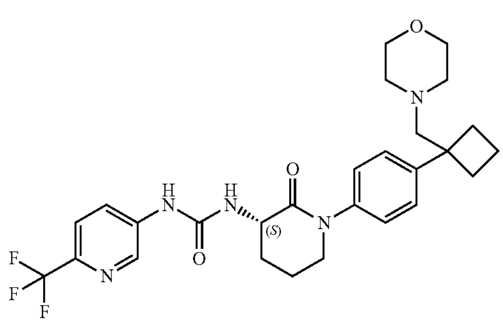 | (S)-1-(1-(4-(1-(morpholinomethyl)cyclobutyl)phenyl)-2-oxopipendin-3-yl)-3-(6-(trifluoromethyl)pyridin-3-yl)urea | 532.3 | Method F, RT = 1.796 min, 99.2% | ¹H NMR (400 MHz, DMSO-d6): δ 9.42 (s, 1H), 8.66 (s, 1H), 8.13 (d, J = 6.4 Hz, 1H), 7.76 (d, J = 8.6 Hz, 1H), 7.25-7.10 (m, 4H), 6.81 (d, J = 6.8 Hz, 1H), 4.38-4.25 (m, 1H), 3.41-3.33 (m, 6H), 2.59 (s, 2H), 2.21-2.07 (m, 9H), 2.02-1.95 (m, 3H), 1.86-1.64 (m, 2H). |

-continued

| Ex | Structure | Name | LCMS (M + H)+ | HPLC Method, RT (min.) & Purity | ¹H NMR |
|---|---|---|---|---|---|
| 63 | 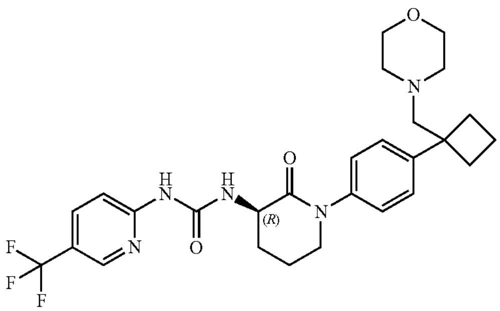 | (R)-1-(1-(4-(1-(morpholinomethyl) cyclobutyl)phenyl)-2-oxopiperidin-3-yl)-3-(5-(trifluoromethyl) pyridin-2-yl)urea | 532.3 | Method F, RT = 1.936 min, 100% | ¹H NMR (400 MHz, DMSO-d6): δ 9.76 (s, 1H), 8.53 (s, 1H), 8.19 (br. s., 1H), 8.03 (dd, J = 8.8, 2.2 Hz, 1H), 7.66 (d, J = 8.8 Hz, 1H), 7.23-7.16 (m, 4H), 4.41-4.32 (m, 1H), 3.73-3.66 (m, 2H), 3.38 (d, J = 4.9 Hz, 4H), 2.60 (s, 2H), 2.32-2.26 (m, 1H), 2.24-2.08 (m, 8H), 2.05-1.92 (m, 3H), 1.85-1.69 (m, 2H). |
| 64 | 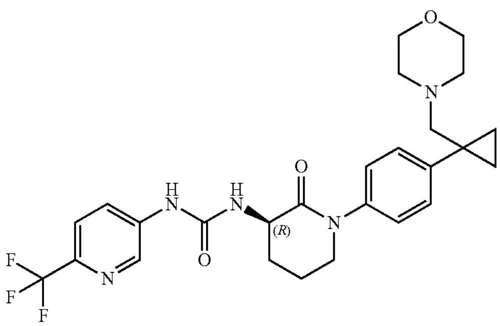 | (R)-1-(1-(4-(1-(morpholinomethyl) cyclopropyl) phenyl)-2-oxopiperidin-3-yl)-3-(6-(trifluoromethyl) pyridin-3-yl)urea | 518.3 | Method F, RT = 1.601 min, 99.25% | ¹H NMR (400 MHz, DMSO-d6): δ 9.43 (s, 1H), 8.67 (d, J = 2.4 Hz, 1H), 8.13 (d, J = 8.1 Hz, 1H), 7.76 (d, J = 8.6 Hz, 1H), 7.35 (d, J = 8.3 Hz, 2H), 7.18 (d, J = 8.3 Hz, 2H), 6.81 (d, J = 6.4 Hz, 1H), 4.37-4.23 (m, 1H), 3.71-3.61 (m, 2H), 3.55-3.42 (m, 4H), 2.51 (s, 2H), 2.43-2.33 (m, 4H), 2.28-2.20 (m, 1H), 2.03-1.91 (m, 2H), 1.82-1.80 (m, 1H), 0.83-0.77 (m, 2H), 0.76-0.71 (m, 2H). |
| 65 | 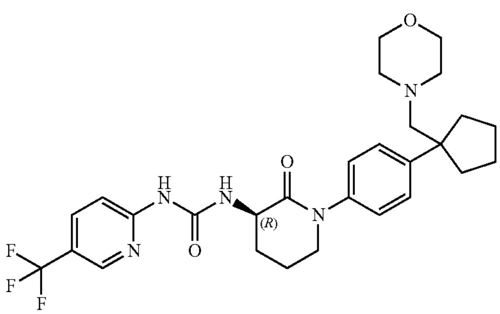 | (R)-1-(1-(4-(1-(morpholinomethyl) cyclopentyl) phenyl)-2-oxopiperidin-3-yl)-3-(5-(trifluoromethyl) pyridin-2-yl)urea | 546.3 | Method F, RT = 2.119 min, 99.4% | ¹H NMR (400 MHz, DMSO-d6): δ 9.77 (s, 1H), 8.54 (s, 1H), 8.15 (d, J = 6.4 Hz, 1H), 8.04 (d, J = 8.3 Hz, 1H), 7.69 (d, J = 9.3 Hz, 1H), 7.30 (d, J = 8.3 Hz, 2H), 7.16 (d, J = 8.3 Hz, 2H), 4.41-4.35 (m, 1H), 3.73-3.66 (m, 2H), 3.39 (d, J = 3.4 Hz, 4H), 2.38 (s, 2H), 2.36-2.30 (m, 1H), 2.10-2.02 (m, 4H), 2.01-1.95 (m, 4H), 1.85-1.50 (m, 7H). |
| 66 | 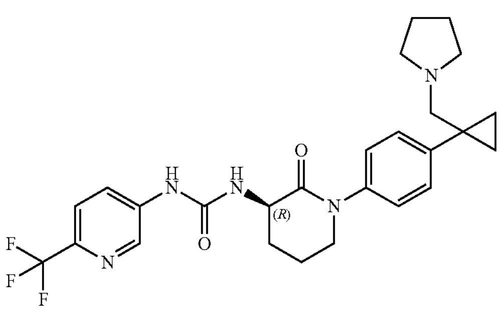 | (R)-1-(2-oxo-1-(4-(1-(pyrrolidin-1-ylmethyl) cyclopropyl)phenyl) piperidin-3-yl)-3-(6-(trifluoromethyl) pyridin-3-yl)urea | 502.3 | Method F, RT = 1.228 min, 100% | ¹H NMR (400 MHz, DMSO-d6): δ 9.43 (s, 1H), 8.67 (d, J = 2.7 Hz, 1H), 8.13 (d, J = 8.6 Hz, 1H), 7.76 (d, J = 8.6 Hz, 1H), 7.39-7.25 (d, J = 8.3 Hz, 2H), 7.23-7.08 (d, J = 8.3 Hz, 2H), 6.81 (d, J = 7.1 Hz, 1H), 4.35-4.24 (m, 1H), 3.69-3.62 (m, 2H), 2.61 (s, 2H), 2.51-2.40 (m., 4H), 2.30-2.22 (m, 1H), 2.00-1.91 (m, 2H), 1.86-1.77 (m, 1H), 1.64-1.57 (m, 4H), 0.83-0.76 (m, 2H), 0.76-0.68 (m, 2H). |
| 67 | 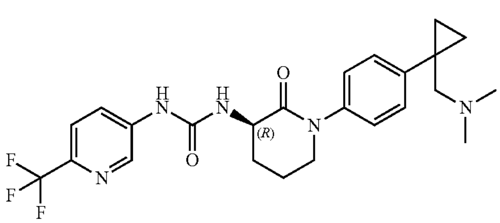 | (R)-1-(1-(4-(1-((dimethylamino) methyl)cyclopropyl) phenyl)-2-oxopiperidin-3-yl)-3-(6-(trifluoromethyl) pyridin-3-yl)urea | 476.3 | Method F, RT = 1.198 min, 98.9% | ¹H NMR (400 MHz, DMSO-d6): δ 9.43 (s, 1H), 8.67 (d, J = 2.2 Hz, 1H), 8.12 (d, J = 8.6 Hz, 1H), 7.76 (d, J = 8.6 Hz, 1H), 7.33 (d, J = 8.3 Hz, 2H), 7.15 (d, J = 8.3 Hz, 2H), 6.81 (d, J = 6.8 Hz, 1H), 4.36-4.26 (m, 1H), 3.66-3.62 (m, 2H), 2.47 (s, 2H), 2.31-2.25 (m, 1H), 2.13 (s, 6H), 2.01-1.90 (m, 2H), 1.81-1.80 (m, 1H), 0.85-0.79 (m, 2H), 0.73-0.68 (m, 2H). |

Example 68: N-((1-(4-((3R,5R)-3-(3-(3-Fluoro-5-(trifluoromethyl)pyridin-2-yl)ureido)-5-hydroxy-2-oxopiperidin-1-yl)phenyl)cyclopropyl)methyl)methanesulfonamide

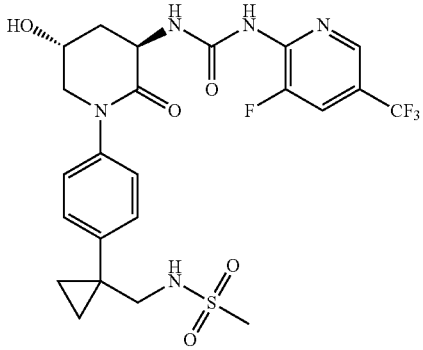 [SMILES: CS(=O)(=O)NCC1(c2ccc(N3C[C@H](O)C[C@@H](NC(=O)Nc4ncc(C(F)(F)F)cc4F)C3=O)cc2)CC1]

Example 68A: trans-5-((tert-butoxycarbonyl)amino)-6-oxopiperidin-3-yl acetate tert-Butyl trans-5-hydroxy-2-oxopiperidin-3-yl)carbamate was synthesized using the procedures found in Gordon, Sandra et al, Farmaco, 52(10), 603-608; 1997. Acetic anhydride (20 mL, 210 mmol) was added to a solution of tert-butyl trans-(5-hydroxy-2-oxopiperidin-3-yl)carbamate (8.0 g, 35 mmol) in pyridine (20 mL) at rt, and the reaction mixture was stirred for 12 h under nitrogen atmosphere. The mixture was concentrated under reduced pressure to give Example 68A (8.0 g, 29 mmol, 85% yield) as a white solid.

Example 68B: trans-5-((tert-Butoxycarbonyl)amino)-1-(4-(1-cyanocyclopropyl)phenyl)-6-oxopiperidin-3-yl acetate To a stirred solution of Example 68A (500 mg, 1.8 mmol) in 1,4-dioxane (4 mL), were added 1-(4-bromophenyl)cyclopropane-1-carbonitrile (410 mg, 1.8 mmol), and $Cs_2CO_3$ (1200 mg, 3.7 mmol). The reaction mixture was purged with nitrogen for 5 min and charged with Xantphos (110 mg, 0.18 mmol) and $Pd_2(dba)_3$ (84 mg, 0.092 mmol). The reaction mixture was again purged with nitrogen for 3 min and heated at 110° C. for 16 h. The reaction mixture was cooled, filtered through a Celite pad, and the filtrate was concentrated under reduced pressure. The crude product was purified using column chromatography (EtOAc-Pet ether) to afford Example 68B (250 mg, 0.61 mmol, 33% yield) as a brown solid. MS (ES) m/z: 414.6 [M+H]+; $^1$H NMR (400 MHz, $CDCl_3$): 7.36-7.30 (m, 2H), 7.30-7.23 (m, 2H), 5.61 (br. s., 1H), 5.30-5.21 (m, 1H), 4.29 (d, J=6.3 Hz, 1H), 3.97 (dd, J=14.4, 3.3 Hz, 1H), 3.77 (dd, J=14.4, 2.6 Hz, 1H), 3.18-3.06 (m, 1H), 2.07 (s, 3H), 1.79-1.71 (m, 2H), 1.71-1.60 (m, 1H), 1.47 (s, 9H), 1.43-1.39 (m, 2H).

Example 68C: trans-tert-butyl (1-(4-(1-(aminomethyl)cyclopropyl)phenyl)-5-hydroxy-2-oxopiperidin-3-yl)carbamate To a stirred solution of Example 68B (250 mg, 0.605 mmol) in MeOH (5 mL), was added Raney nickel (160 mg, 1.8 mmol). The reaction mixture was stirred under hydrogen atmosphere (70 psi) at rt for an hour. The resulting mixture was filtered through a syringe filter and concentrated under reduced pressure. The crude residue was triturated with hexane (2×10 mL) to afford Example 68C (200 mg, 0.53 mmol, 88% yield). MS(ESI) m/z: 376.6 (M+H)+; $^1$H NMR (400 MHz, DMSO-d6): δ 7.30 (d, J=8.0 Hz, 2H), 7.25-7.16 (m, 2H), 5.18 (br. s., 1H), 4.18-4.05 (m, 2H), 3.77-3.68 (m, 1H), 3.44 (dd, J=12.5, 5.5 Hz, 1H), 3.17 (s, 2H), 2.82-2.65 (m, 2H), 2.33-2.28 (m, 1H), 1.77-1.65 (m, 1H), 1.38 (s, 9H), 0.86-0.66 (m, 4H).

Example 68D: trans-tert-butyl (1-(4-(1-(aminomethyl)cyclopropyl)phenyl)-5-((tert-butyldimethylsilyl)oxy)-2-oxopiperidin-3-yl)carbamate Imidazole (45 mg, 0.67 mmol) and TBDMS-Cl (100 mg, 0.67 mmol) were added to a stirred solution of Example 68C (250 mg, 0.67 mmol) in DCM (2 mL). The reaction mixture was stirred at rt for additional 12 hours. The reaction mixture was evaporated, and the residue was washed with EtOAc (3×5 mL). The combined organic layer was evaporated to give Example 68D (250 mg, 0.510 mmol, 77% yield). MS (ES) m/z: 490.7 [M+H]+.

Example 68E: trans-tert-butyl (5-((tert-butyldimethylsilyl)oxy)-1-(4-(1-(methylsulfonamidomethyl)cyclopropyl)phenyl)-2-oxopiperidin-3-yl)carbamate To a stirred solution Example 68D (230 mg, 0.47 mmol) in DCM (2 mL) at 0° C., were added TEA (0.20 mL, 1.4 mmol) and mesylchloride (0.044 mL, 0.56 mmol). The reaction mixture was gradually warmed to room temperature and stirred for an additional 1 hour. The reaction mixture was quenched with water (10 mL), and extracted with DCM (2×20 mL). The combined organic layers were washed with brine (20 mL), dried over $Na_2SO_4$ and concentrated under reduced pressure. The crude residue was triturated with pet ether (20 mL) to afford Example 68E (230 mg, 0.405 mmol, 86% yield). MS(ESI) m/z: 568.7 (M+H)+. $^1$H NMR (400 MHz, $CDCl_3$): (δ 7.40-7.34 (m, 2H), 7.32-7.28 (m, 2H), 5.62 (br. s., 1H), 4.24 (br. s., 2H), 3.80 (d, J=3.5 Hz, 1H), 3.57 (dd, J=13.6, 3.5 Hz, 1H), 3.29 (d, J=6.0 Hz, 2H), 2.87 (d, J=7.5 Hz, 1H), 2.77 (s, 3H), 1.65 (d, J=12.5 Hz, 1H), 1.47 (s, 9H), 0.97-0.86 (m, 13H), 0.09 (d, J=9.0 Hz, 6H).

Example 68F: trans-N-((1-(4-(3-amino-5-hydroxy-2-oxopiperidin-1-yl)phenyl)cyclopropyl)methyl)methanesulfonamide hydrochloride To an ice cooled solution of Example 68E (230 mg, 0.41 mmol) in 1,4-dioxane (2 mL), was added 4 N HCl in 1,4-dioxane (2 mL, 8 mmol), and the mixture was stirred at rt for two hours. The solvent was evaporated and dried under reduced pressure to obtain a gummy solid. The solid was triturated with diethyl ether (2×20 ml) and dried to afford Example 68F (140 mg, 0.396 mmol, 98% yield). MS(ESI) m/z: 354.6 (M+H)+; $^1$H NMR (400 MHz, DMSO-d6): (δ 8.40 (d, J=4.5 Hz, 2H), 7.40-7.32 (m, 2H), 7.29-7.21 (m, 2H), 7.08 (t, J=6.3 Hz, 1H), 4.24-4.17 (m, 3H), 3.79-3.75 (m, 1H), 3.55-3.50 (m, 1H), 3.22-3.14 (m, 2H), 2.73 (s, 3H), 2.59-2.53 (m, 1H), 1.82-1.78 (m, 1H), 0.95-0.76 (m, 4H).

Example 68

To an ice cooled solution of Example 68F (80 mg, 0.23 mmol) in DMSO (2 mL) under nitrogen, were added $K_2CO_3$ (63 mg, 0.45 mmol) and phenyl (3-fluoro-5-(trifluoromethyl)pyridin-2-yl)carbamate (82 mg, 0.27 mmol). The reaction mixture was gradually warmed up to rt and stirred for 15 hours. The reaction mixture was filtered through a syringe filter and concentrated under reduced pressure. The crude product was purified by reverse phase chromatography followed by chiral HPLC to afford Example 68 (6.0 mg, 11 μmol, 4.7% yield). RT=1.33 min, 99% (Method F); MS(ESI) m/z: 560.2 (M+H)+; $^1$H NMR (400 MHz, DMSOd6): (δ 9.65 (s, 1H), 9.26 (d, J=7.6 Hz, 1H), 8.42 (s, 1H), 8.11 (d, J=12.5 Hz, 1H), 7.32 (d, J=8.3 Hz, 2H), 7.17 (d, J=8.3 Hz, 2H), 7.01 (t, J=6.1 Hz, 1H), 5.55 (d, J=3.2 Hz, 1H), 4.73-4.69 (m, 1H), 4.42-4.36 (m, 1H), 4.22-4.17 (m, 1H), 3.81-3.75 (m, 1H), 3.17 (d, J=5.1 Hz, 2H), 2.72 (s, 4H), 2.19-2.12 (m, 1H), 0.94-0.84 (m, 2H), 0.81-0.71 (m, 2H).

Example 69: N-((1-(4-((3S,5S)-3-(3-(3-fluoro-5-(trifluoromethyl)pyridin-2-yl)ureido)-5-hydroxy-2-oxopiperidin-1-yl)phenyl)cyclopropyl)methyl)methanesulfonamide

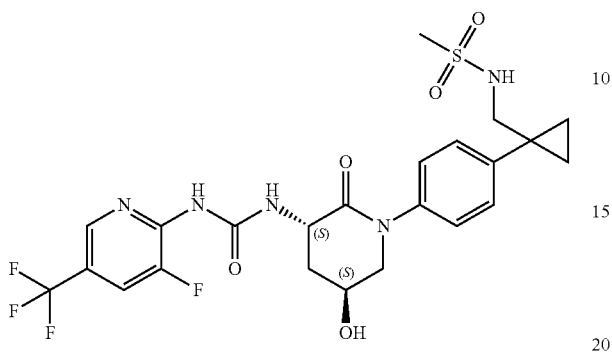

Example 69 was also isolated from the synthesis of Example 68. Method F, RT=1.327 min, 100%. MS(ESI) m/z: 560.2 (M+H)$^+$; 1H NMR (400 MHz, DMSO-d6): δ 9.75 (br. s., 1H), 9.19 (d, J=6.8 Hz, 1H), 8.43 (s, 1H), 8.16 (s, 1H), 8.19 (s, 1H), 7.33 (d, J=8.1 Hz, 2H), 7.21 (d, J=8.3 Hz, 2H), 7.05 (t, J=6.0 Hz, 1H), 5.37 (d, J=3.4 Hz, 1H), 4.80-4.67 (m, 1H), 4.21-4.17 (m, 1H), 4.13 (d, J=4.6 Hz, 1H), 3.87 (dd, J=12.5, 3.7 Hz, 1H), 3.17 (d, J=6.0 Hz, 2H), 2.72 (s, 3H), 2.19-1.14 (m., 2H), 0.92-0.87 (m, 2H), 0.83-0.75 (m, 2H).

Additional examples of compounds of this invention shown in Table 3 below were prepared using combinations of the procedures described in Example 1 and 68 or modifications thereof known to one skilled in the art of organic synthesis. Table 3. Racemization can occur during the synthesis that can be separated at the final stage with chiral chromatography to give all possible stereoisomers.

| Ex. | Structure | LCMS (M + H)+ | HPLC Method, RT (min.) & Purity | $^1$H NMR |
|---|---|---|---|---|
| 70 | N-((1-(4-((3R,5R)-3-(3-(5-chloro-3-fluoropyridin-2-yl)ureido)-5-hydroxy-2-oxopiperidin-1-yl)phenyl)cyclopropyl)methyl)methanesulfonamide | 526.2 | Method F, RT = 1.156 min, 100% | $^1$H NMR (400 MHz, DMSO-d6): δ 9.39 (br. s., 1H), 8.93 (br. s., 1H), 8.14 (d, J = 2.2 Hz, 1H), 8.01 (m, 1H), 7.33 (d, J = 8.6 Hz, 2H), 7.25 (d, J = 8.3 Hz, 2H), 7.05 (t, J = 6.0 Hz, 1H), 5.24 (br. s., 1H), 4.50-4.39 (m, 1H), 4.21-4.17 (m, 1H), 4.13 (d, J = 5.6 Hz, 1H), 3.87-3.80 (m, 1H), 3.17 (d, J = 6.0 Hz, 2H), 2.72 (s, 3H), 1.65-1.58 (m, 1H), 1.16-1.09 (m, 1H), 0.92-0.87 (m, 2H), 0.83-0.75 (m, 2H). |

| Ex. | Structure | LCMS (M + H)+ | HPLC Method, RT (min.) & Purity | ¹H NMR |
|---|---|---|---|---|
| 71 | 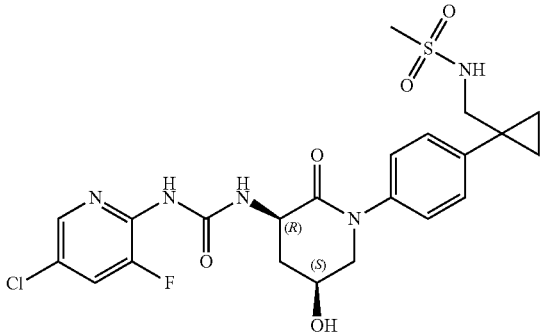<br>N-((1-(4-((3R,5R)-3-(3-(5-chloro-3-fluoropyridin-2-yl)ureido)-5-hydroxy-2-oxopiperidin-1-yl)phenyl)cyclopropyl)methyl)methanesulfonamide | 526.2 | Method F, RT = 1.156 min, 100% | ¹H NMR (400 MHz, DMSO-d6): δ 9.39 (s, 1H), 8.93 (d, J = 6.6 Hz, 1H), 8.15 (d, J = 2.0 Hz, 1H), 8.01 (dd, J = 9.9, 2.1 Hz, 1H), 7.35 (d, J = 8.6 Hz, 2H), 7.28 (d, J = 8.6 Hz, 2H), 7.05 (t, J = 5.9 Hz, 1H), 5.26 (d, J = 3.9 Hz, 1H), 4.47-4.42 (m, 1H), 4.23-4.19 (m, 1H), 4.16-4.05 (m, 1H), 3.85 (d, J = 9.8 Hz, 1H), 3.18 (d, J = 5.9 Hz, 2H), 2.74 (m, 4H), 1.65-1.58 (m, 1H),), 0.93-0.88 (m, 2H), 0.83-0.76 (m, 2H). |

Additional examples of compounds of this invention shown in Table 4 below were prepared using combinations of procedure described in the previous examples or modifications thereof known to one skilled in the art of organic synthesis. Racemization can occur during the synthesis that can be separated at the final stage with chiral chromatography to give all possible stereoisomers.

| Ex | Structure | IUPAC Name | LCMS (M + H)+ | HPLC Method, RT (min) & Purity | ¹H NMR |
|---|---|---|---|---|---|
| 72 | 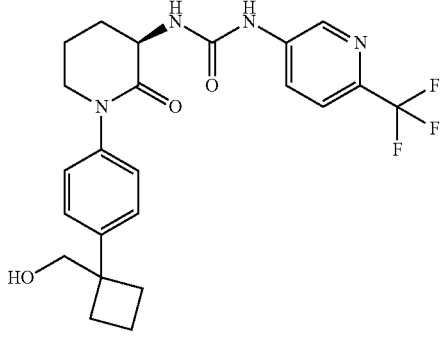 [SMILES: O=C(Nc1ccc(C(F)(F)F)nc1)N[C@@H]1CCCN(c2ccc(C3(CO)CCC3)cc2)C1=O] | (R)-1-(1-(4-(1-(Hydroxymethyl)cyclobutyl)phenyl)-2-oxopiperidin-3-yl)-3-(6-(trifluoromethyl)pyridin-3-yl)urea | 463.2 | Method F, RT = 1.603 min, 98.9% | ¹H NMR (400 MHz, DMSO-d₆) δ 9.48 (s, 1H), 8.69 (d, J = 2.4 Hz, 1H), 8.15 (dd, J = 8.4, 2.6 Hz, 1H), 7.77 (d, J = 8.6 Hz, 1H), 7.26-7.17 (m, 2H), 7.16-7.11 (m, 2H), 6.86 (d, J = 6.8 Hz, 1H), 4.80 (t, J = 5.3 Hz, 1H), 4.41-4.28 (m, 1H), 3.70-3.64 (m, 2H), 3.56-2.50 (m, 2H), 2.33-2.12 (m, 5H), 2.04-1.92 (m, 3H), 1.85-1.69 (m, 2H). |

| Ex | Structure | IUPAC Name | LCMS (M + H)+ | HPLC Method, RT (min) & Purity | ¹H NMR |
|---|---|---|---|---|---|
| 73 | 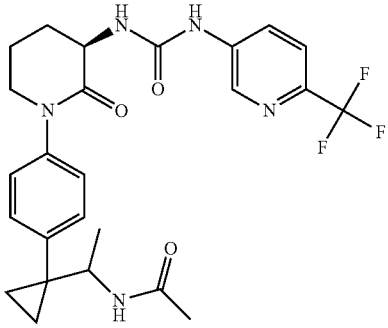 (Homochiral) | N-(1-(1-(4-((R)-2-Oxo-3-(3-(6-(trifluoromethyl)pyridin-3-yl)ureido)piperidin-1-yl)phenyl)cyclopropyl)ethyl))acetamide | 504.3 | Method F, RT = 1.518 min, 98.8% | ¹H NMR (400 MHz, DMSO-$d_6$) δ 9.42 (s, 1H), 8.67 (d, J = 2.4 Hz, 1H), 8.12 (d, J = 6.4 Hz, 1H), 7.77 (d, J = 8.6 Hz, 1H), 7.57 (d, J = 9.0 Hz, 1H), 7.30 (d, J = 8.6 Hz, 2H), 7.22 (d, J = 8.3 Hz, 2H), 6.82 (d, J = 7.1 Hz, 1H), 4.37-4.28 (m, 1H), 3.70-3.63 (m, 2H), 2.74-2.70 (m, 1H), 2.28-2.20 (m, 1H), 2.08 (s, 3H), 2.04-2.95 (m, 2H), 1.85-1.74 (m, 1H), 0.97 (d, J = 6.8 Hz, 3H), 0.73-0.50 (m, 4H). |
| 74 | 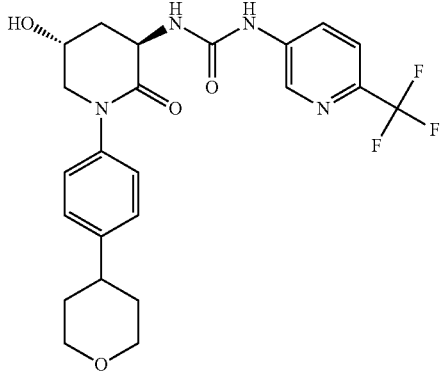 [SMILES: O=C(Nc1ccc(C(F)(F)F)nc1)N[C@@H]1C[C@@H](O)CN(c2ccc(C3CCOCC3)cc2)C1=O] | 1-((3R,5R)-5-Hydroxy-2-oxo-1-(4-(tetrahydro-2H-pyran-4-yl)phenyl)piperidin-3-yl)-3-(4-(trifluoromethyl)phenyl)urea | 478.2 | Method F, RT = 1.551 min, 98.8% | ¹H NMR (400 MHz, DMSO-$d_6$) δ 9.21 (s, 1H), 7.70-7.51 (m, 4H), 7.34-7.25 (m, 2H), 7.24-7.14 (m, 2H), 6.62 (d, J = 7.3 Hz, 1H), 5.33 (d, J = 3.4 Hz, 1H), 4.60 (m, 1H), 4.24-4.16 (m, 1H), 4.03-3.92 (m, 2H), 3.86 (dd, J = 12.6, 4.3 Hz, 1H), 3.52 (dd, J = 12.1, 3.8 Hz, 1H), 3.44 (td, J = 11.0, 3.4 Hz, 2H), 2.77 (m, 1H), 2.28-2.20 (m, 1H), 2.14-2.05 (m, 1H), 1.78-1.59 (m, 4H). |
| 75 | 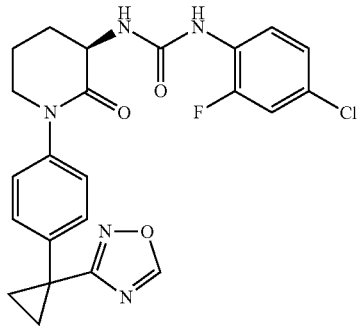 [SMILES: O=C(Nc1ccc(Cl)cc1F)N[C@@H]1CCCN(c2ccc(C3(c4ncon4)CC3)cc2)C1=O] | (R)-1-(1-(4-(1-(1,2,4-Oxadiazol-3-yl)cyclopropyl)phenyl)-2-oxopiperidin-3-yl)-3-(4-chloro-2-fluorophenyl)urea | 470.2 | Method F, RT = 1.748 min, 97.1% | ¹H NMR (400 MHz, DMSO-$d_6$) δ 9.47 (s, 1H), 8.75-8.70 (m, 1H), 8.17 (t, J = 8.9 Hz, 1H), 7.50-7.36 (m, 3H), 7.29 (d, J = 8.6 Hz, 2H), 7.19 (d, J = 9.0 Hz, 1H), 7.12 (d, J = 6.8 Hz, 1H), 4.39-4.30 (m, 1H), 3.76-3.64 (m, 2H), 2.30-2.64 (m, 1H), 2.06-1.90 (m, 2H), 1.85-1.71 (m, 1H), 1.58-1.49 (m, 2H), 1.46-1.35 (m, 2H). |

| Ex | Structure | IUPAC Name | LCMS (M + H)+ | HPLC Method, RT (min) & Purity | ¹H NMR |
|---|---|---|---|---|---|
| 76 | (Homochiral) | 1-(4-Chloro-2-fluorophenyl)-3-((3R)-1-(4-(2-hydroxycyclopentyl)phenyl)-2-oxopiperidin-3-yl)urea | 446.2 | Method F, RT = 1.675 min, 100% | ¹H NMR (400 MHz, DMSO-d₆) δ 8.70 (d, J = 1.5 Hz, 1H), 8.16 (t, J = 8.9 Hz, 1H), 7.40 (dd, J = 11.1, 2.6 Hz, 1H), 7.32-7.23 (m, 2H), 7.23-7.13 (m, 3H), 7.11 (d, J = 7.1 Hz, 1H), 4.73 (d, J = 5.4 Hz, 1H), 4.37-4.28 (m, 1H), 3.97 (m, 1H), 3.71-3.60 (m, 2H), 2.83-2.76 (m, 1H), 2.34-2.28 (m, 1H), 2.10-1.91 (m, 4H), 1.80-1.50 (m, 5H). |
| 77 | (Homochiral) | 1-(4-Chloro-2-fluorophenyl)-3-((3R)-1-(4-(3-hydroxycyclopentyl)phenyl)-2-oxopiperidin-3-yl)urea | 446.2 | Method F, RT = 1.640 min, 100% | ¹H NMR (400 MHz, DMSO-d₆) δ 8.70 (d, J = 2.4 Hz, 1H), 8.16 (t, J = 8.9 Hz, 1H), 7.40 (dd, J = 11.1, 2.3 Hz, 1H), 7.30 (m, J = 8.3 Hz, 2H), 7.23-7.15 (m, 3H), 7.10 (d, J = 6.8 Hz, 1H), 4.63 (d, J = 4.2 Hz, 1H), 4.38-4.26 (m, 1H), 4.26-4.17 (m, 1H), 3.73-3.57 (m, 2H), 3.04-2.91 (m, 1H), 2.36-2.25 (m, 2H), 2.06-1.87 (m, 3H), 1.84-1.59 (m, 4H), 1.55-1.42 (m, 1H). |
| 78 | (Homochiral) | 1-(4-Chloro-2-fluorophenyl)-3-((3R)-1-(4-(3-(dimethylamino)cyclopentyl)phenyl)-2-oxopiperidin-3-yl)urea | 473.2 | Method F, RT = 1.342 min, 94% | ¹H NMR (400 MHz, DMSO-d₆) δ 8.70 (d, J = 2.0 Hz, 1H), 8.16 (t, J = 8.9 Hz, 1H), 7.40 (dd, J = 11.2, 2.4 Hz, 1H), 7.31-7.24 (m, 2H), 7.24-7.12 (m, 3H), 7.10 (d, J = 6.8 Hz, 1H), 4.39-4.25 (m, 1H), 3.73-3.61 (m, 2H), 3.21-3.14 (m, 1H), 3.08-3.04 (m, 1H), 2.46-2.23 (m, 7H), 2.17-1.91 (m, 5H), 1.88-1.70 (m, 2H), 1.67-1.54 (m, 2H). |

| Ex | Structure | IUPAC Name | LCMS (M + H)+ | HPLC Method, RT (min) & Purity | ¹H NMR |
|---|---|---|---|---|---|
| 79 | (Homochiral) | 1-(4-Chloro-2-fluorophenyl)-3-((3R)-1-(4-(4-hydroxytetrahydrofuran-3-yl)phenyl)-2-oxopiperidin-3-yl)urea | 488.2 | Method F, RT = 1.401 min, 100% | ¹H NMR (400 MHz, DMSO-$d_6$) δ 8.70 (d, J = 2.0 Hz, 1H), 8.16 (t, J = 8.9 Hz, 1H), 7.40 (dd, J =11.2, 2.4 Hz, 1H), 7.33-7.21 (m, 4H), 7.18 (m, 1H), 7.10 (d, J = 6.6 Hz, 1H), 5.28 (d, J = 4.6 Hz, 1H), 4.33 (m, 1H), 4.28-4.20 (m, 1H), 4.15 (m, 1H), 3.96 (m, 1H), 3.77-3.60 (m, 3H), 3.57 (dd, J = 9.0, 3.9 Hz, 1H), 3.19 (m, 1H), 2.32-2.27 (m, 1H), 2.06-1.89 (m, 2H), 1.83-1.68 (m, 1H). |
| 80 | (Homochiral) | 1-((3R)-1-(4-(4-Hydroxytetrahydrofuran-3-yl)phenyl)-2-oxopiperidin-3-yl)-3-(4-(trifluoromethyl)phenyl)urea | 464.2 | Method F, RT = 1.511 min, 100% | ¹H NMR (400 MHz, DMSO-$d_6$) δ 9.23 (s, 1H), 7.70-7.50 (m, 4H), 7.38-7.15 (m, 4H), 6.70 (d, J = 6.8 Hz, 1H), 5.28 (d, J = 4.4 Hz, 1H), 4.38-4.28 (m, 1H), 4.28-4.21 (m, 1H), 4.16 (dd, J = 8.7, 7.2 Hz, 1H), 3.97 (dd, J = 9.2, 5.7 Hz, 1H), 3.76-3.60 (m, 3H), 3.59-3.54 (m, 1H), 3.19 (m1H), 2.35-2.26 (m, 1H), 2.07-1.90 (m, 2H), 1.87-1.76 (m, 1H). |

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

The invention claimed is:
1. A compound of formula I

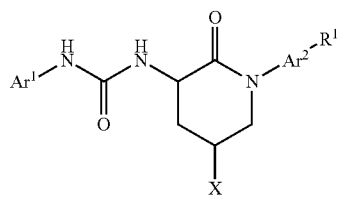

where:
$Ar^1$ is phenyl, pyridinyl, pyridazinyl, pyrimidinyl, pyrazinyl, or benzodioxyl, and is substituted with 1-3 substituents selected from cyano, halo, alkyl, fluoroalkyl, alkoxy, fluoroalkoxy, alkylthio, and alkyl sulfonyl;
$Ar^2$ is phenyl, pyridinyl, pyridazinyl, pyrimidinyl, or pyrazinyl, and is substituted with 0-3 substituents selected from cyano, halo, alkyl, fluoroalkyl, alkoxy, and fluoroalkoxy;
$Ar^3$ is 5- or 6-membered monocyclic heteroaromatic ring system with 1-5 heteroatoms independently selected from nitrogen, oxygen, and sulfur;
$R^1$ is cyclopropyl, cyclobutyl, cyclopentyl, cyclohexyl, tetrahyrofuranyl, or tetrahydropyranyl, and is substituted with 0-2 substituents selected from cyano, alkyl, haloalkyl, hydroxyalkyl, alkoxyalkyl, $((R^2)(R^3)N)$alkyl, hydroxy, alkoxy, $(R^2)(R^3)N$, $(R^2)(R^3)NCO$, and $Ar^3$;
$R^2$ is hydrogen, alkyl, alkylcarbonyl, or alkylsulfonyl;
$R^3$ is hydrogen or alkyl;
or $NR^2R^3$ taken together is selected from azetidinyl, pyrrolidinyl, piperidinyl, piperazinyl, and morpholinyl, and is substituted with 0-3 substituents selected from halo, alkyl, fluoroalkyl, alkoxy, and fluoroalkoxy; and
X is hydrogen, fluoro, hydroxy, or alkoxy;
or a pharmaceutically acceptable salt thereof.

2. A compound of claim 1 where
Ar$^1$ is phenyl, pyrazinyl or pyridinyl and is substituted with 1-3 substituents selected from cyano, halo, alkyl, fluoroalkyl, haloalkyl, alkoxy, fluoroalkoxy, alkylthio, and alkylsulfonyl;
Ar$^2$ is phenyl substituted with 0-3 substituents selected from cyano, halo, alkyl, fluoroalkyl, alkoxy, and haloalkoxy;
R$^1$ is cyclopropyl, cyclobutyl, cyclopentyl, cyclohexyl, tetrahyrofuranyl, or tetrahydropyranyl, and is substituted with 0-2 substituents selected from cyano, alkyl, fluoroalkyl, hydroxyalkyl, alkoxyalkyl, ((R$^2$)(R$^3$)N)alkyl, hydroxy, alkoxy, (R$^2$)(R$^3$)N, (R$^2$)(R$^3$)NCO, and Ar$^3$;
R$^2$ is hydrogen, alkyl, alkylcarbonyl, or alkylsulfonyl;
R$^3$ is hydrogen or alkyl;
or NR$^2$R$^3$ taken together is selected from azetidinyl, pyrrolidinyl, piperidinyl, piperazinyl, and morpholinyl, and is substituted with 0-3 substituents selected from fluoro, alkyl, fluoroalkyl, alkoxy, and haloalkoxy; and
X is hydrogen, fluoro, hydroxy, or alkoxy;
or a pharmaceutically acceptable salt thereof.

3. A compound of claim 1 where Ar$^1$ is phenyl, pyrazinyl or pyridinyl and is substituted with 1-3 substituents selected from cyano, halo, alkyl, fluoroalkyl, alkoxy, fluoroalkoxy, alkylthio, and alkylsulfonyl.

4. A compound of claim 1 where Ar$^2$ is phenyl substituted with 0-3 substituents selected from cyano, halo, alkyl, haloalkyl, alkoxy, and fluroalkoxy.

5. A compound of claim 1 where cyclopropyl, cyclobutyl, cyclopentyl, cyclohexyl, tetrahyrofuranyl, or tetrahydropyranyl, and is substituted with 0-2 substituents selected from cyano, ((R$^2$)(R$^3$)N)alkyl, and hydroxy.

6. A composition comprising a compound of claim 1, or a pharmaceutically acceptable salt thereof, and a pharmaceutically acceptable carrier, diluent, or excipient.

7. A method treating heart failure comprising administering a therapeutically effective amount of a compound of claim 1 to a patient in need thereof.

* * * * *